US009999406B2

(12) United States Patent
Hibner et al.

(10) Patent No.: US 9,999,406 B2
(45) Date of Patent: Jun. 19, 2018

(54) BIOPSY DEVICE TISSUE SAMPLE HOLDER WITH REMOVABLE TRAY

(75) Inventors: John A. Hibner, Mason, OH (US); John S. Ehlert, Cincinnati, OH (US); James A. McCrea, San Carlos, CA (US)

(73) Assignee: Devicor Medical Products, Inc., Cincinnati, OH (US)

( * ) Notice: Subject to any disclaimer, the term of this patent is extended or adjusted under 35 U.S.C. 154(b) by 792 days.

(21) Appl. No.: 13/226,660

(22) Filed: Sep. 7, 2011

(65) Prior Publication Data

US 2012/0065542 A1 Mar. 15, 2012

Related U.S. Application Data

(60) Provisional application No. 61/381,466, filed on Sep. 10, 2010.

(51) Int. Cl.
*A61B 10/02* (2006.01)

(52) U.S. Cl.
CPC ...... *A61B 10/0275* (2013.01); *A61B 10/0283* (2013.01); *A61B 2010/0225* (2013.01)

(58) Field of Classification Search
CPC ........ A61B 10/0096; A61B 2010/0208; A61B 2010/0225; A61B 10/0266–10/0283; B01L 3/50
USPC ................................................ 600/562–568
See application file for complete search history.

(56) References Cited

U.S. PATENT DOCUMENTS

| | | | |
|---|---|---|---|
| 5,526,822 A | 6/1996 | Burbank et al. | |
| 6,068,544 A | 5/2000 | Chiu | |
| 6,228,055 B1 | 5/2001 | Foerster et al. | |
| 6,371,904 B1 | 4/2002 | Sirimanne et al. | |
| 6,485,436 B1 | 11/2002 | Truckai et al. | |

(Continued)

FOREIGN PATENT DOCUMENTS

| | | |
|---|---|---|
| AU | 2011299267 B2 | 5/2015 |
| CN | 2406615 Y | 11/2000 |

(Continued)

OTHER PUBLICATIONS

International Search Report and Written Opinion dated Apr. 23, 2012 for Application No. PCT/US2011/050626.

(Continued)

*Primary Examiner* — Rene Towa
*Assistant Examiner* — H. Q. Nguyen
(74) *Attorney, Agent, or Firm* — Frost Brown Todd LLC

(57) ABSTRACT

A biopsy device comprises a body, a needle, a cutter, and a tissue sample holder. The tissue sample holder comprises an outer cup and a cap. A tray retains severed tissue samples from a biopsy procedure. In some versions, the tray is selectively detachable from the cap in a one-handed operation by the user. The tray may be ejected into a sample container, such as a formalin cup. The cap may include a threaded portion that is configured to engage a complementary threaded portion of a sample container to seal the sample container once the tissue samples have been transferred to the sample container from the tissue sample holder of the biopsy device. One or more ports may be provided in the cap to manage excess fluid within the outer cup of the tissue sample holder, and/or to provide integrated access for a marker delivery device.

18 Claims, 27 Drawing Sheets

(56) References Cited

U.S. PATENT DOCUMENTS

| | | |
|---|---|---|
| 6,626,849 B2 | 9/2003 | Huitema et al. |
| 6,993,375 B2 | 1/2006 | Burbank et al. |
| 6,996,433 B2 | 2/2006 | Burbank et al. |
| 7,044,957 B2 | 5/2006 | Foerster et al. |
| 7,047,063 B2 | 5/2006 | Burbank et al. |
| 7,229,417 B2 | 6/2007 | Foerster et al. |
| 7,442,171 B2 | 10/2008 | Stephens et al. |
| 7,465,279 B2 | 12/2008 | Beckman et al. |
| 7,819,800 B2 | 10/2010 | Beckman et al. |
| 7,854,706 B2 | 12/2010 | Hibner |
| 7,918,804 B2 | 4/2011 | Monson et al. |
| 8,475,394 B1 * | 7/2013 | Stivers .................. 600/572 |
| D695,404 S | 12/2013 | Horning et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 2006/0074345 A1 | 4/2006 | Hibner |
| 2007/0032740 A1 | 2/2007 | Quick et al. |
| 2007/0255175 A1 * | 11/2007 | Sangha ............ A61B 10/0045 |
| | | 600/572 |
| 2008/0019778 A1 * | 1/2008 | Godoy ............... A44B 11/2592 |
| | | 405/186 |
| 2008/0134810 A1 * | 6/2008 | Neel ...................... B01L 3/545 |
| | | 73/866 |
| 2008/0146882 A1 | 6/2008 | Crapper et al. |
| 2008/0195066 A1 | 8/2008 | Speeg et al. |
| 2008/0214955 A1 | 9/2008 | Speeg et al. |
| 2009/0131817 A1 | 5/2009 | Speeg et al. |
| 2009/0137928 A1 | 5/2009 | Quick et al. |
| 2009/0209854 A1 | 8/2009 | Parihar et al. |
| 2009/0270725 A1 | 10/2009 | Leimbach et al. |
| 2009/0294397 A1 * | 12/2009 | Wu ............................... 215/6 |
| 2010/0049084 A1 | 2/2010 | Nock et al. |
| 2010/0106053 A1 * | 4/2010 | Videbaek ........... A61B 10/0096 |
| | | 600/564 |
| 2010/0152610 A1 | 6/2010 | Parihar et al. |
| 2010/0160816 A1 | 6/2010 | Parihar et al. |
| 2010/0160819 A1 | 6/2010 | Parihar et al. |
| 2010/0160824 A1 | 6/2010 | Parihar et al. |
| 2010/0160826 A1 | 6/2010 | Parihar |
| 2010/0317997 A1 | 12/2010 | Hibner et al. |
| 2011/0071391 A1 | 3/2011 | Speeg |
| 2011/0071423 A1 | 3/2011 | Speeg et al. |
| 2011/0071424 A1 | 3/2011 | Nock et al. |
| 2011/0071431 A1 | 3/2011 | Speeg et al. |
| 2011/0201964 A1 | 8/2011 | Speeg et al. |
| 2011/0208086 A1 | 8/2011 | Hibner et al. |
| 2011/0208090 A1 | 8/2011 | Parihar |
| 2011/0218433 A1 | 9/2011 | Speeg et al. |
| 2012/0283563 A1 | 11/2012 | Moore et al. |

FOREIGN PATENT DOCUMENTS

| | | |
|---|---|---|
| CN | 101543415 A | 9/2009 |
| EP | 1642534 A2 | 4/2006 |
| JP | 5905888 B2 | 4/2016 |
| WO | WO 1998/033436 | 8/1998 |
| WO | WO 2000/030531 | 6/2000 |
| WO | WO 2006/131423 A1 | 12/2006 |
| WO | WO 2007/019445 | 2/2007 |
| WO | WO 2007/120865 | 10/2007 |
| WO | WO 2008/040812 | 4/2008 |

OTHER PUBLICATIONS

Japanese Office Action dated Aug. 13, 2015 for Application No. JP 2013-528260.
Australian Patent Examination Report No. 1 dated Mar. 26, 2014 for Application No. AU2011299267.
Chinese First Office Action dated Jun. 13, 2014 for Application No. CN201180043795.9.
Chinese Second Office Action dated Feb. 13, 2015 for Application No. CN201180043795.9.
Chinese Third office Action dated Sep. 7, 2015 for Application No. CN201180043795.9.
Chinese Fourth Office Action dated Mar. 22, 2016 for Application No. 2011800437959, 11 pgs.
Extended European Search Report dated Dec. 13, 2016 for Application No. 11824044.9, 7 pages.
Canadian Office Action dated Apr. 10, 2017 for Application No. 2,808,310, 4 pages.

* cited by examiner

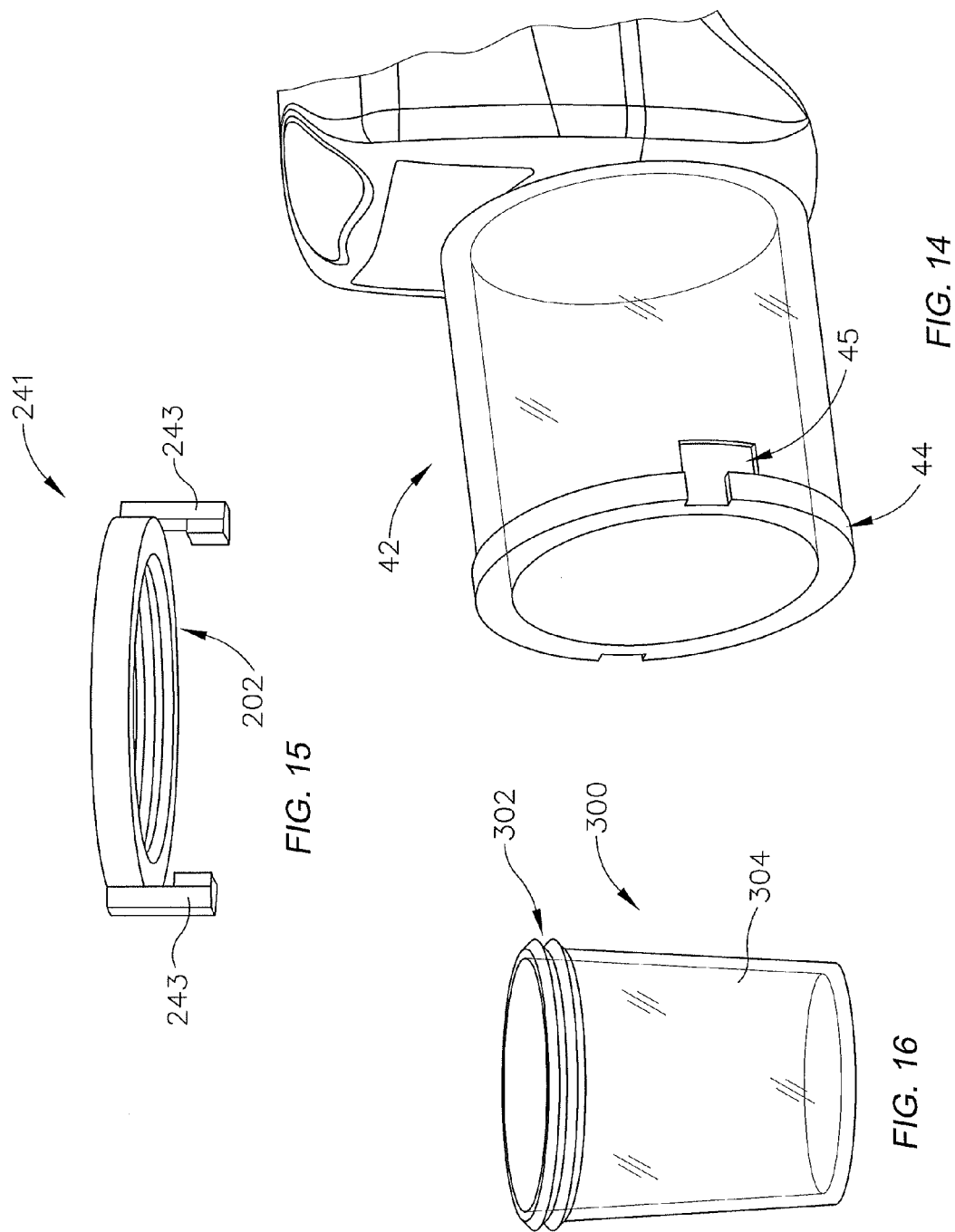

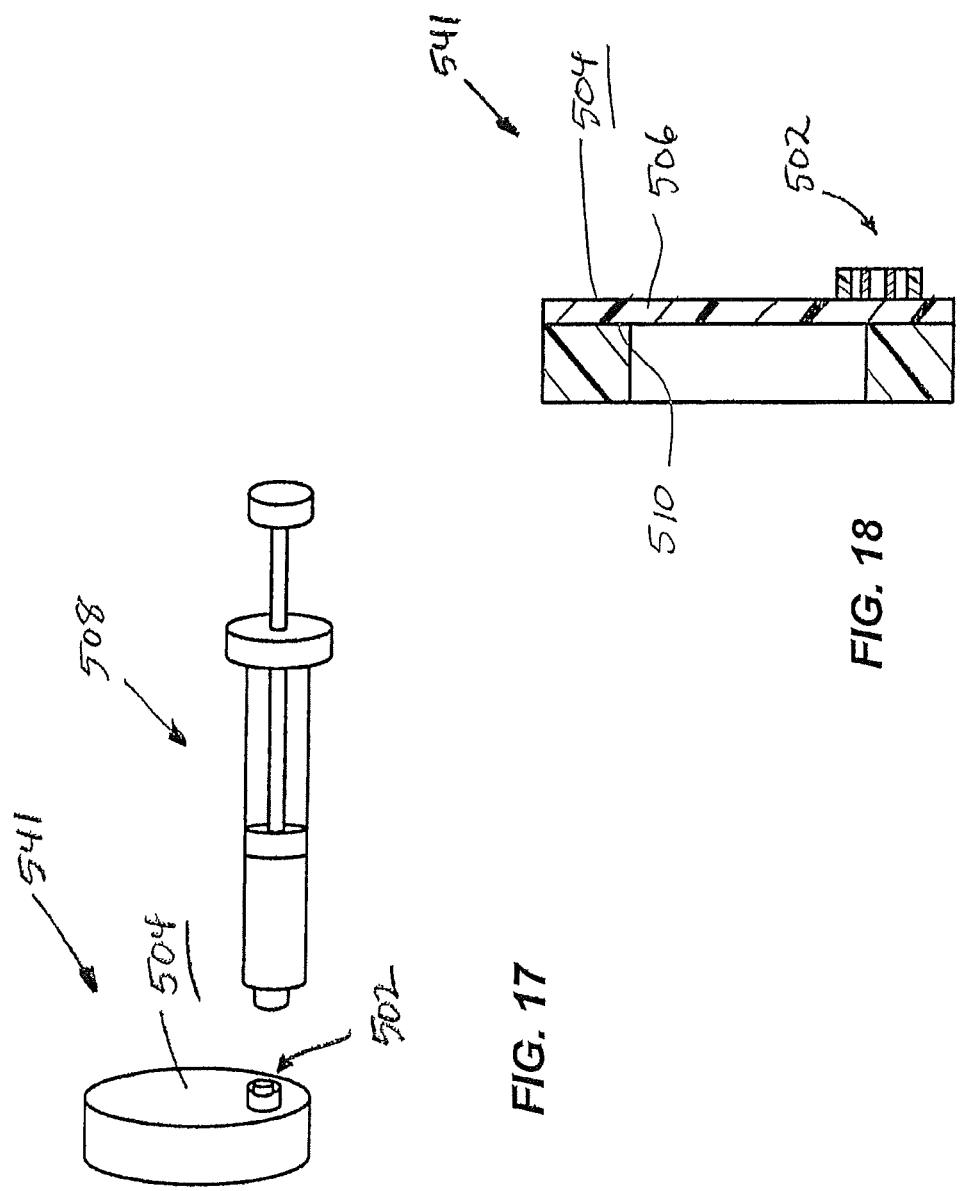

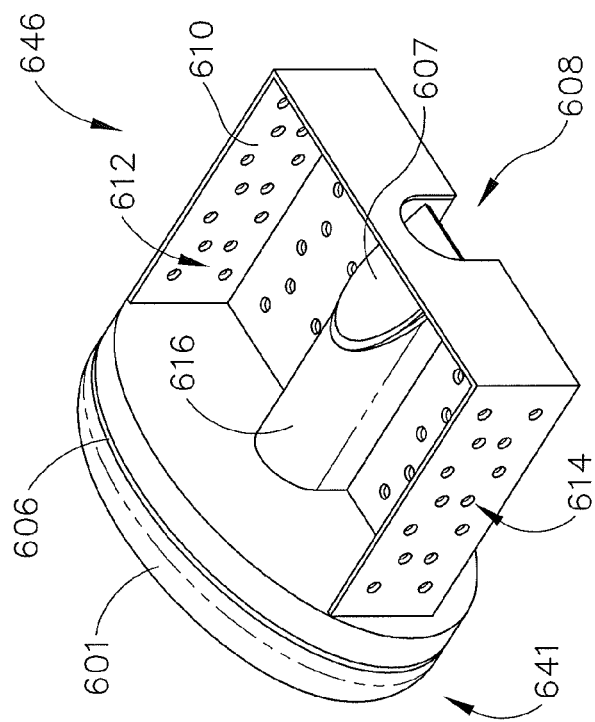
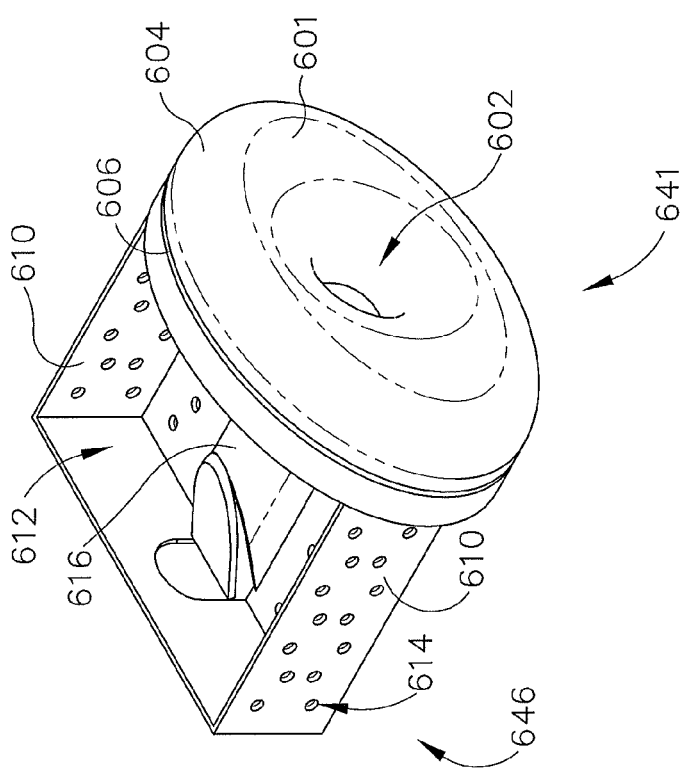

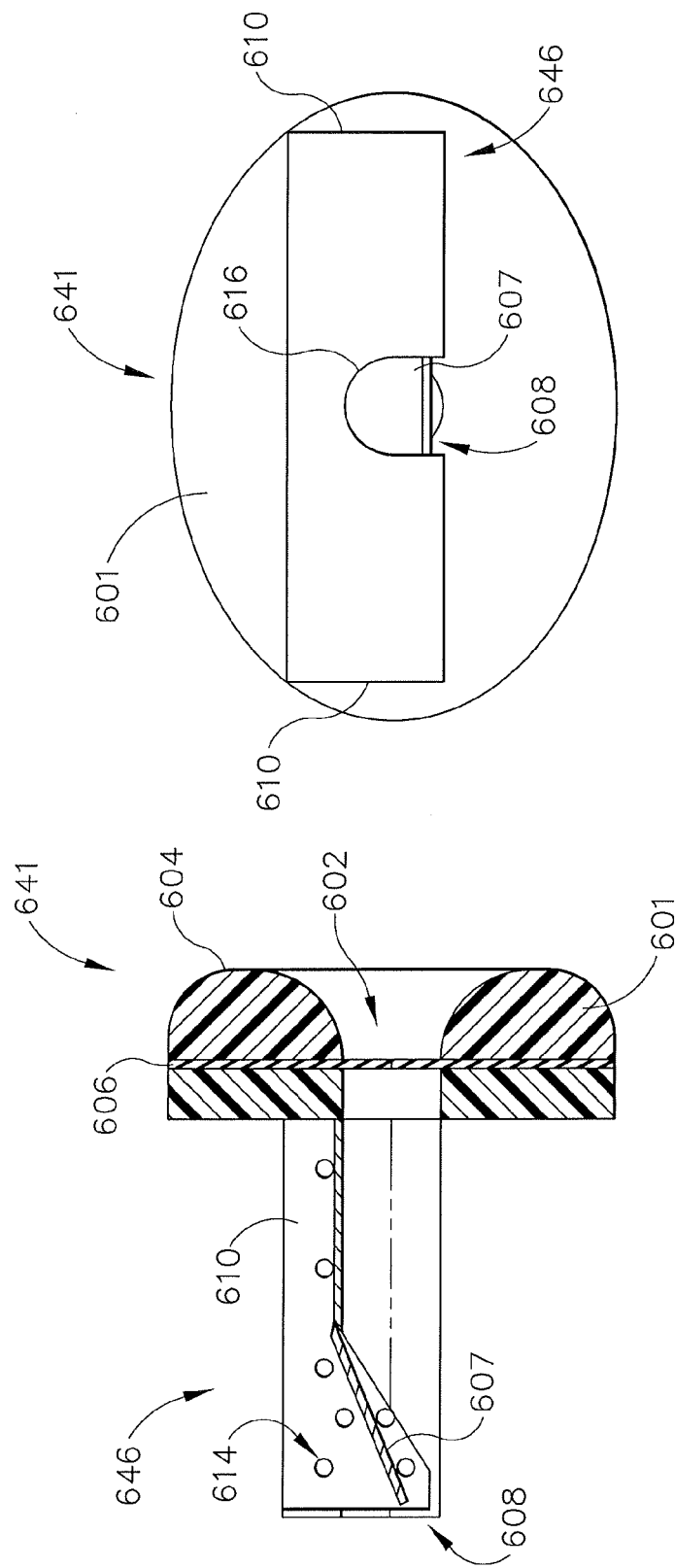

BIOPSY DEVICE TISSUE SAMPLE HOLDER WITH REMOVABLE TRAY

PRIORITY

This application claims priority to U.S. Provisional Application Ser. No. 61/381,466, filed Sep. 10, 2010, entitled "Biopsy Device Tissue Sample Holder with Removable Basket," the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 30, 2003; U.S. Pub. No. 2006/0074345, entitled "Biopsy Apparatus and Method," published Apr. 6, 2006; U.S. Pat. No. 7,442,171, entitled "Remote Thumbwheel for a Surgical Biopsy Device," issued Oct. 28, 2008; U.S. Pub. No. 2008/0214955, entitled "Presentation of Biopsy Sample by Biopsy Device," published Sep. 4, 2008; U.S. Pat. No. 7,854,706, entitled "Clutch and Valving System for Tetherless Biopsy Device," issued Dec. 21, 2010; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; U.S. patent application Ser. No. 12/953,715, entitled "Handheld Biopsy Device with Needle Firing," filed Nov. 24, 2010; U.S. patent application Ser. No. 13/086,567, entitled "Biopsy Device with Motorized Needle Firing," filed Apr. 14, 2011; U.S. patent application Ser. No. 13/099,497, entitled "Biopsy Device with Manifold Alignment Feature and Tissue Sensor," filed May 3, 2011; U.S. patent application Ser. No. 13/150,950, entitled "Needle Assembly and Blade Assembly for Biopsy Device," filed Jun. 1, 2011; and U.S. patent application Ser. No. 13/205,189, entitled "Access Chamber and Markers for Biopsy Device," filed Aug. 8, 2011. The disclosure of each of the above-cited U.S. Patents, U.S. Patent Application Publications, and U.S. Non-Provisional Patent Applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary devices and methods for marking a biopsy site are disclosed in U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pub. No. 2011/0071431, entitled "Biopsy Marker Delivery Device," published Mar. 24, 2011; U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,465,279, entitled "Marker Device and Method of Deploying a Cavity Marker Using a Surgical Biopsy Device," issued Dec. 16, 2008; and U.S. patent application Ser. No. 13/205,189, entitled "Access Chamber and Markers for Biopsy Device," filed Aug. 8, 2011. The disclosure of each of the above-cited U.S. Patents, U.S. Patent Application Publications, and U.S. Patent Applications is incorporated by reference herein.

While several systems and methods have been made and used for obtaining a biopsy sample and marking the sample location, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

FIG. 14 depicts a perspective view of an exemplary outer cup of a tissue sample holder;

FIG. 15 depicts a perspective view of an exemplary cap of a tissue sample holder;

FIG. 16 depicts a perspective view of an exemplary sample container;

FIG. 17 depicts an exemplary cap for a tissue sample holder, with the cap having a port for fluid management;

FIG. 18 depicts a cross-sectional view of the cap of FIG. 17;

FIG. 19 depicts a perspective view of an exemplary tray and cap of a tissue sample holder;

FIG. 20 depicts another perspective view of the tray and cap of FIG. 19;

FIG. 21 depicts a cross-sectional view of the tray and cap of FIG. 19;

FIG. 22 depicts a front view of the tray and cap of FIG. 19, shown from the tray end;

Figure 1:
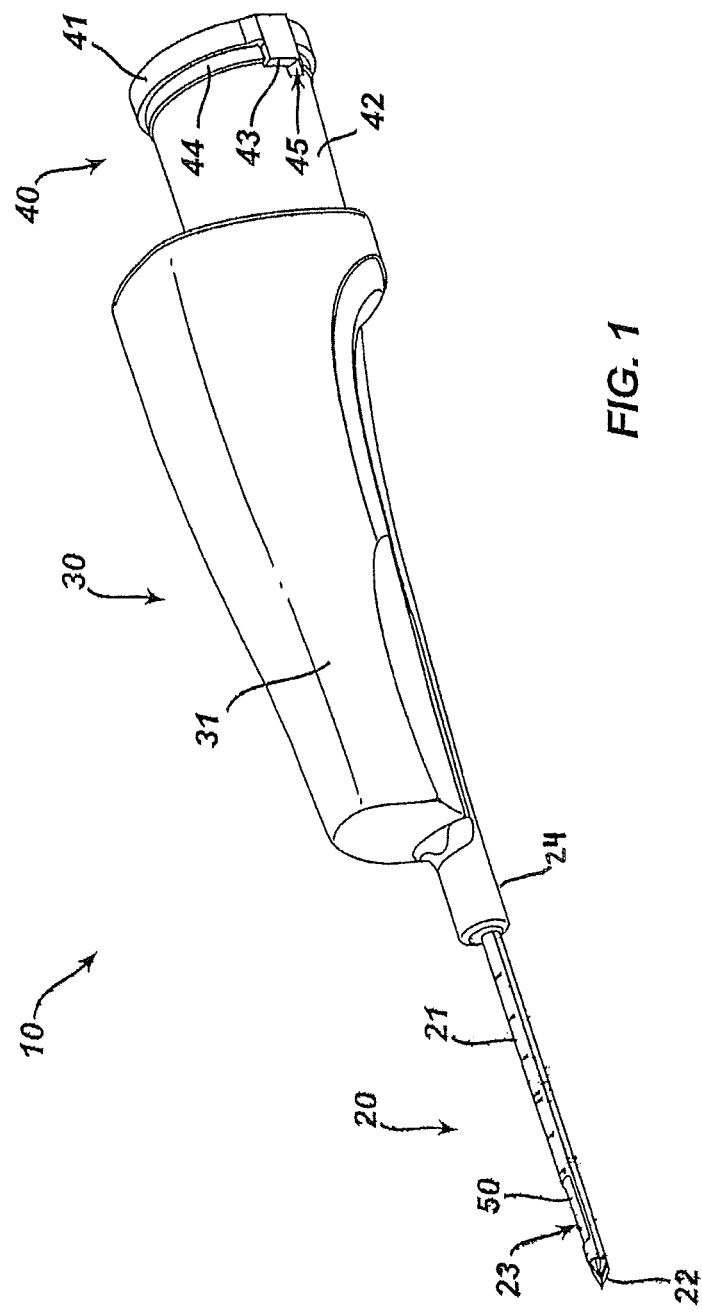
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview

A. Exemplary Biopsy Device

As shown in FIG. 1, an exemplary biopsy device (10) comprises a needle (20), a body (30), a tissue sample holder (40), and a cutter (50). In particular, needle (20) extends distally from the distal portion of body (30), while tissue sample holder (40) extends proximally from the proximal portion of body (30). Body (30) is sized and configured such that biopsy device (10) may be operated by a single hand of a user. In particular, a user may grasp body (30), insert needle (20) into a patient's breast, and collect one or a plurality of tissue samples from within the patient's breast, all with just using a single hand. Alternatively, a user may grasp body (30) with more than one hand and/or with any desired assistance. In some settings, the user may capture a plurality of tissue samples with just a single insertion of needle (20) into the patient's breast. Such tissue samples may be pneumatically deposited in tissue sample holder (40), and later retrieved from tissue sample holder (40) for analysis. While examples described herein often refer to the acquisition of biopsy samples from a patient's breast, it should be understood that biopsy device (10) may be used in a variety of other procedures for a variety of other purposes and in a variety of other parts of a patient's anatomy.

Needle (20) of the present example comprises a cannula (21) with a tissue piercing tip (22), a lateral aperture (23), and a hub (24). Tissue piercing tip (22) is configured to pierce and penetrate tissue, without requiring a high amount of force, and without requiring an opening to be pre-formed in the tissue prior to insertion of tip (22). Alternatively, tip (22) may be blunt (e.g., rounded, flat, etc.) if desired. Lateral aperture (23) is sized to receive a tissue from a tissue specimen during operation of device (10). Within cannula (21) resides cutter (50), which rotates and translates relative to cannula (21) and past lateral aperture (23) to sever a tissue sample from tissue protruding through lateral aperture (23). Hub (24) may be formed of plastic that is overmolded about needle (20) or otherwise secured to needle (20), such that hub (24) is unitarily secured to needle (20). Alternatively, hub (24) may be formed of any other suitable material through any suitable process and may have any other suitable relationship with needle (20). Hub (24) of the present example is coupled with a vacuum conduit (not shown), and is operable to communicate a vacuum (or atmospheric air, saline, pressurized fluid, etc.) from vacuum conduit to lateral aperture (23). The vacuum conduit may be coupled with a variety of sources, including but not limited to a vacuum source that is internal or external to biopsy device (10) in accordance with the teachings of U.S. Pub. No. 2010/0317997, entitled "Tetherless Biopsy Device with Reusable Portion," published Dec. 16, 2010, and/or U.S. Pub. No. 2008/0214955, entitled "Presentation of Biopsy Sample by Biopsy Device," published Sep. 4, 2008, the disclosures of which are incorporated by reference herein. Still other suitable fluid sources that a vacuum conduit may be coupled with will be apparent to those of ordinary skill in the art in view of the teachings herein. Of course, any suitable type of valve(s) and/or switching mechanism(s) may also be coupled with vacuum conduit, e.g., as taught in U.S. Pub. No. 2010/0317997, entitled "Tetherless Biopsy Device with Reusable Portion," published Dec. 16, 2010, and/or U.S. Pub. No. 2008/0214955, entitled "Presentation of Biopsy Sample by Biopsy Device," published Sep. 4, 2008, the disclosures of which are incorporated by reference herein. It should also be understood that a vacuum, atmospheric air, a liquid such as saline, etc. may also be selectively communicated to the lumen defined by cutter (50).

Body (30) of the present example comprises a housing (31). In some versions, body (30) is formed in at least two pieces, comprising a probe portion and a holster portion. For instance, in some such versions, the probe portion may be separable from the holster portion. Furthermore, the probe portion may be provided as a disposable component while the holster portion may be provided as a reusable portion. By way of example only, such a probe and holster configuration may be provided in accordance with the teachings of U.S. Pub. No. 2010/0317997, entitled "Tetherless Biopsy Device with Reusable Portion," published Dec. 16, 2010, and/or U.S. Pub. No. 2008/0214955, entitled "Presentation of Biopsy Sample by Biopsy Device," published Sep. 4, 2008, and/or U.S. patent application Ser. No. 12/953,715, entitled "Handheld Biopsy Device with Needle Firing," filed Nov. 24, 2010, the disclosures of which are incorporated by reference herein. Alternatively, any other suitable probe and holster configuration may be used. It should also be understood that body (30) may be configured such that it does not have a separable probe portion and holster portion. Various other suitable ways in which body (30) may be configured will be apparent to those of ordinary skill in the art in view of the teachings herein.

Tissue sample holder (40) of the present example comprises a cap (41) and an outer cup (42). As will be described in greater detail below, a tray (46) (shown in FIGS. 10-13) is provided within outer cup (42). Cup (42) is secured to body (30) in the present example. Such engagement may be provided in any suitable fashion. Outer cup (42) of the present example is substantially transparent, allowing the user to view tissue samples on tray (46), though outer cup (42) may have any other suitable properties if desired.

The hollow interior of outer cup (42) is in fluid communication with cutter (50) and with a vacuum source (70) in the present example. Thus, when a tissue sample has been severed from a tissue specimen by cutter (50), the tissue sample is pulled from cutter (50) to tissue sample holder (40) by vacuum. In the present example, and as will be described in greater detail below, vacuum source (70) may be within body (30) or external to body (30). By way of example only, vacuum may be provided to outer cup (42), and such a vacuum may be further communicated to cutter (50), in accordance with the teachings of U.S. Pub. No. 2010/0317997, entitled "Tetherless Biopsy Device with Reusable Portion," published Dec. 16, 2010, and/or U.S. patent application Ser. No. 12/953,715, entitled "Handheld Biopsy Device with Needle Firing," filed Nov. 24, 2010, the disclosures of which are incorporated by reference herein. As another merely illustrative example, vacuum may be provided to outer cup (42) from an external vacuum source (70) in accordance with the teachings of U.S. Pub. No. 2008/0214955, entitled "Presentation of Biopsy Sample by Biopsy Device," published Sep. 4, 2008, the disclosure of which is incorporated by reference herein. Various other suitable ways in which vacuum may be provided to outer cup (42) will be apparent to those of ordinary skill in the art in view of the teachings herein. It should also be understood that outer cup (42) may receive vacuum from the same vacuum source (70) as the vacuum conduit in needle (20). Biopsy device (10) may further include one or more valves (e.g., shuttle valve, electromechanical solenoid valve, etc.) to selectively regulate communication of a vacuum and/or other fluids to outer cup (42) and/or vacuum conduit, regardless of whether outer cup (42) and vacuum conduit are coupled with a common source of vacuum or other source of fluid.

Cap (41) is removably coupled with outer cup (42) in the present example such that a user may remove cap (41) to access tissue samples that have been gathered on the tray (46) within outer cup (42) during a biopsy process. A pair of latches (43) provide selective engagement between cap (41) and outer cup (42). In particular, latches (43) engage a lip (44) of outer cup (42). Lip (44) has gaps (45) permitting passage of latches (43), such that a user may secure cap (41) to outer cup (42) by aligning latches (43) with gaps (45), pushing cap (41) onto outer cup (42), then rotating cap (41) past gaps (45) to engage latches (43) with lip (44). Alternatively, cap (41) may be secured to outer cup (42) in any other suitable fashion (e.g., latches (43) having resilient properties and/or living hinges to permit engagement of latches (43) with lip (44), etc.). An o-ring (not shown) provides a seal when cap (41) is engaged with outer cup (42). A vacuum may thus be maintained within outer cup (42) when cap (41) is secured to outer cup (42). In operation, a user may remove cap (41) to access tissue samples that have gathered on a tray (46) within outer cup (42) during a biopsy process. In the present example, cap (41) is removed by rotating cap (41) to align latches (43) with gaps (45), then pulling cap (41) off. Of course, cap (41) may be removed from outer cup (42) in any other suitable fashion.

Tissue sample holder (40) of the present example is configured to hold at least ten tissue samples. Alternatively, tissue sample holder (40) may be configured to hold any other suitable number of tissue samples. It should be understood that, as with other components described herein, tissue sample holder (40) may be varied, modified, substituted, or supplemented in a variety of ways; and that tissue sample holder (40) may have a variety of alternative features, components, configurations, and functionalities. For instance, tissue sample holder (40) may be alternatively configured such that, in lieu of having a stationary tray (46), tissue sample holder (40) may have a plurality of trays or compartments that are removably coupled with a rotatable manifold, such that the manifold is operable to successively index each tray or compartment relative to cutter (50) to separately receive tissue samples obtained in successive cutting strokes of cutter (50). For instance, tissue sample holder (40) may be constructed and operable in accordance with the teachings of U.S. Pub. No. 2008/0214955, entitled "Presentation of Biopsy Sample by Biopsy Device," published Sep. 4, 2008, the disclosure of which is incorporated by reference herein. Such indexing may be provided automatically or manually. By way of example only, tissue sample holder (40) may be configured and operable in accordance with the teachings of U.S. Pub. No. 2008/0195066, entitled "Revolving Tissue Sample Holder for Biopsy Device," published Aug. 14, 2008, the disclosure of which is incorporated by reference herein; U.S. Pub. No. 2010/0160826, entitled "Tissue Biopsy Device with Rotatably Linked Thumbwheel and Tissue Sample Holder," published Jun. 24, 2010; U.S. Pub. No. 2010/0160824, entitled "Biopsy Device with Discrete Tissue Chambers," published Jun. 24, 2010, the disclosure of which is incorporated by reference herein; or U.S. Pub. No. 2010/0160816, entitled "Mechanical Tissue Sample Holder Indexing Device," published Jun. 24, 2010, the disclosure of which is incorporated by reference herein. In some other versions, tissue sample holder (40) is configured in accordance with the teachings of U.S. Pub. No. 2010/0317997, entitled "Tetherless Biopsy Device with Reusable Portion," published Dec. 16, 2010, the disclosure of which is incorporated by reference herein. Other suitable alternative versions, features, components, configurations, and functionalities of tissue sample holder (40) will be apparent to those of ordinary skill in the art in view of the teachings herein.

It should be understood that, as with other components described herein, needle (20), body (30), tissue sample holder (40), and cutter (50) may be varied, modified, substituted, or supplemented in a variety of ways, and that needle (20), body (30), tissue sample holder (40), and cutter (50) may have a variety of alternative features, components, configurations, and functionalities. Several merely exemplary variations, modifications, substitutions, or supplementations are described in U.S. Non-Provisional patent application Ser. No. 12/709,624, entitled "Spring Loaded Biopsy Device," filed Feb. 22, 2010, the disclosure of which is hereby incorporated by reference. Still yet, other suitable alternative versions, features, components, configurations, and functionalities of needle (20), body (30), tissue sample holder (40), and cutter (50) will be apparent to those of ordinary skill in the art in view of the teachings herein.

Figure 2:
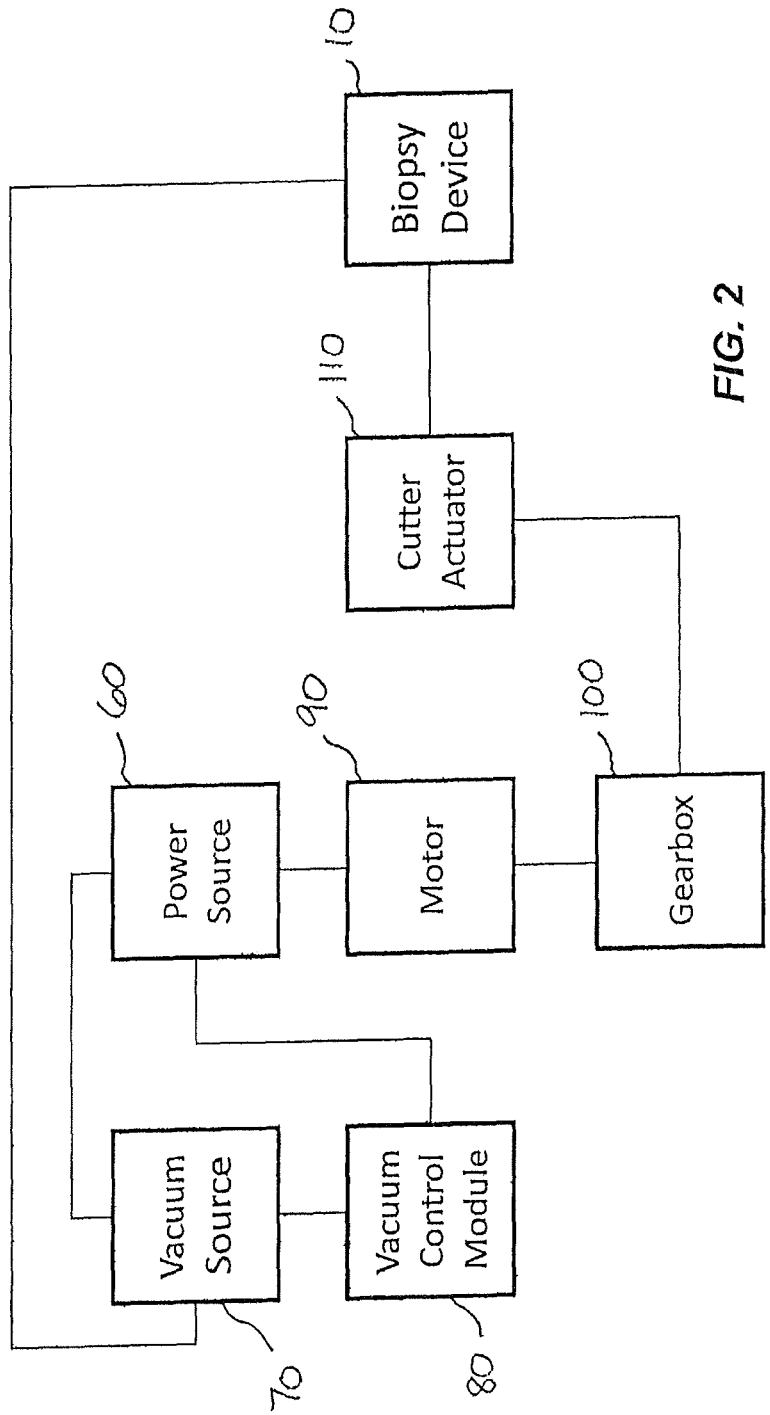
FIG. 2 depicts a block schematic view of components that are part of, or used with, the device of FIG. 1.

As shown in FIG. 2, exemplary components that are part of, or used with, the device of FIG. 1, some of which have been introduced above, include a power source (60), a vacuum source (70), a vacuum control module (80), a motor (90), a set of gears (100), and a cutter actuator (110). In the present example, power source (60) provides power to vacuum source (70), vacuum control module (80), and motor (90). In some versions, power source (60) is located onboard biopsy device (10), e.g., a battery; while in some other versions, power source (60) is located some distance from biopsy device (10), e.g., line voltage from a standard electrical receptacle with a cable connection to biopsy device (10) and/or through an additional module between an electrical receptacle and biopsy device (10). Various configurations for and modifications to power source (60) will be apparent to those of ordinary skill in the art in view of the teachings herein.

In the present example, vacuum source (70) provides vacuum to biopsy device (10) for drawing tissue into lateral aperture (23) of needle (20). Vacuum source (70) also provides vacuum to biopsy device (10) for transporting a severed tissue sample from cutter (50) to tissue sample holder (40). In some versions, vacuum source (70) comprises a vacuum pump located onboard biopsy device (10). By way of example only, such an onboard vacuum source (70) may comprise a diaphragm pump that is driven by motor (90). In some such versions, vacuum source (70) is not coupled with power source (60) and vacuum control module (80) is omitted. In some other versions, vacuum source (70) comprises a vacuum pump located some distance from biopsy device (10) that provides vacuum via a vacuum cable or conduit. Of course, vacuum source (70) may comprise a combination of a vacuum pump located within housing (31) and a vacuum pump that is external to housing (31), if desired. In the present example, vacuum source (70) is in communication with vacuum control module (80). Vacuum control module (80) includes functions to control the supply and delivery of vacuum from vacuum source (70) to biopsy device (10). Various functions and capabilities that can be used with vacuum control module (80) to control how vacuum is supplied and delivered will be apparent to those of ordinary skill in the art in view of the teachings herein. Also, various other configurations for, and modifications to, vacuum source (70) and vacuum control module (80) will be apparent to those of ordinary skill in the art based on the teachings herein.

Motor (90) of the present example comprises a conventional DC motor, though it should be understood that any other suitable type of motor may be used. By way of example only, motor (90) may comprise a pneumatic motor (e.g., having an impeller, etc.) that is powered by pressurized air, a pneumatic linear actuator, an electromechanical linear actuator, a piezoelectric motor (e.g., for use in MRI settings), or a variety of other types of movement-inducing devices. As mentioned above, motor (90) receives power from power source (60). In some versions, motor (90) is located onboard biopsy device (10) (e.g., within housing (31)). In some other versions, motor (90) is located some distance from biopsy device (10) and provides energy to biopsy device (10) via a drive shaft or cable. In the present example, motor (90) is operable to rotate a drive shaft (not shown), which extends distally from motor (90) to gear set (100) to provide a rotary input into gear set (100). While the drive shaft extends directly from motor (90) into gear set (100), it should be understood that a variety of other components may be coupled between motor (90) and gear set (100), including but not limited to various gears, a clutch, etc. Gear set (100) includes an output shaft (not shown) having a drive gear (not shown) secured thereto, and is operable to selectively activate cutter actuator (110). Gear set (100) may comprise a planetary gearbox, and may be configured to provide speed reduction. Various suitable configurations for motor (90) and gear set (100) will be apparent to those of ordinary skill in the art in view of the teachings herein.

Cutter actuator (110) of the present example comprises a variety of components that interact to provide simultaneous rotation and distal translation of cutter (50) relative to body (30) and needle (20) in a firing stroke. Cutter actuator (110) is also operable to retract cutter (50) proximally to ready cutter (50) for firing. By way of example only, cutter actuator (110) may be configured and operable in accordance with the teachings of U.S. Non-Provisional patent application Ser. No. 12/709,624, entitled "Spring Loaded Biopsy Device," filed Feb. 22, 2010, and/or U.S. Pub. No. 2008/0214955, entitled "Presentation of Biopsy Sample by Biopsy Device," published Sep. 4, 2008, the disclosures of which are incorporated by reference herein. It should be understood that, as with other components described herein, cutter actuator (110) may be varied, modified, substituted, or supplemented in a variety of ways, and that cutter actuator (110) may have a variety of alternative features, components, configurations, and functionalities. Suitable alternative versions, features, components, configurations, and functionalities of cutter actuator (110) will be apparent to those of ordinary skill in the art in view of the teachings herein.

Figure 3:
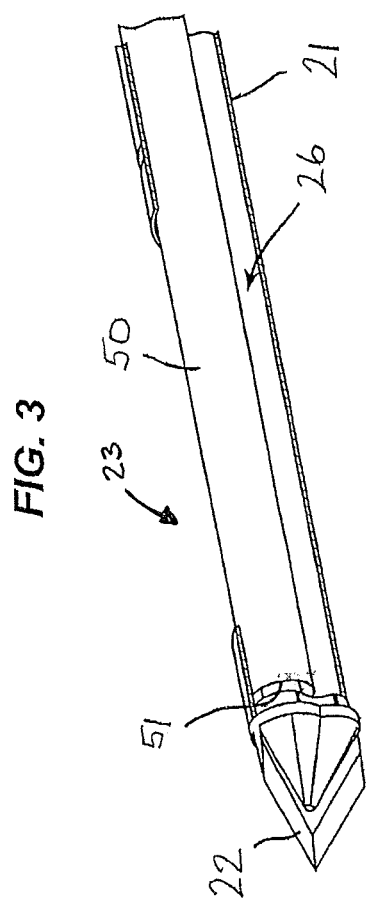
FIG. 3 depicts a first series view of part of the needle of the biopsy device of FIG. 1, with the needle shown in cross section and with the cutter in the initial, distal position.
Figure 4:
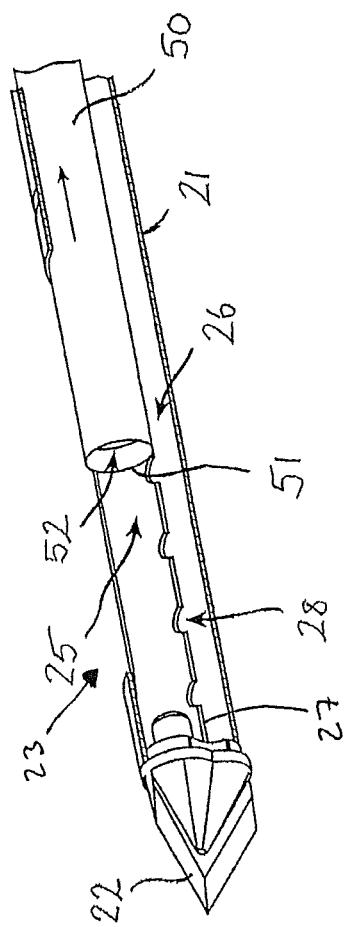
FIG. 4 depicts a second series view of part of the needle of the biopsy device of FIG. 1, with the needle shown in cross section and with the cutter in an intermediate position during retraction.

As shown in the series views of FIGS. 3-6, an exemplary cutter (50) firing sequence is shown. FIG. 3 depicts cutter (50) in a distal position, with distal edge (51) of cutter (50) positioned distal of lateral aperture (23) thereby effectively "closing" lateral aperture (23) of needle (20). In this configuration, needle (20) can be inserted without tissue prolapsing through lateral aperture (23). FIG. 4 depicts cutter (50) being retracted by cutter actuator (110), thereby exposing tissue to lateral aperture (23) and revealing a cutter lumen (52) of cutter (50). In the present example, cutter (50) is positioned within a first lumen (25) of cannula (21). Beneath first lumen (25) is a second lumen (26), which is in part defined by a divider (27). Divider (27) comprises a plurality of openings (28) that provide fluid communication between first and second lumens (25, 26). A plurality of external openings (not shown) may also be formed in needle (20), and may be in fluid communication with second lumen (26). For instance, such external openings may be configured in accordance with the teachings of U.S. Pat. No. 7,918,804, entitled "Biopsy Device with Vacuum Assisted Bleeding Control," issued Apr. 5, 2011, the disclosure of which is incorporated by reference herein. Cutter (50) may also include one or more side openings (not shown). Of course, as with other components described herein, such external openings in needle (20) and cutter (50) are merely optional.

Figure 5:
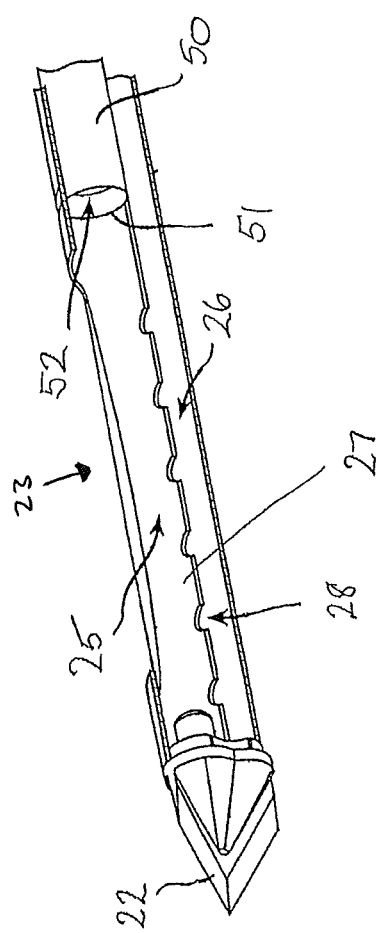
FIG. 5 depicts a third series view of part of the needle of the biopsy device of FIG. 1, with the needle shown in cross section and with the cutter in the retracted, proximal position.
Figure 6:
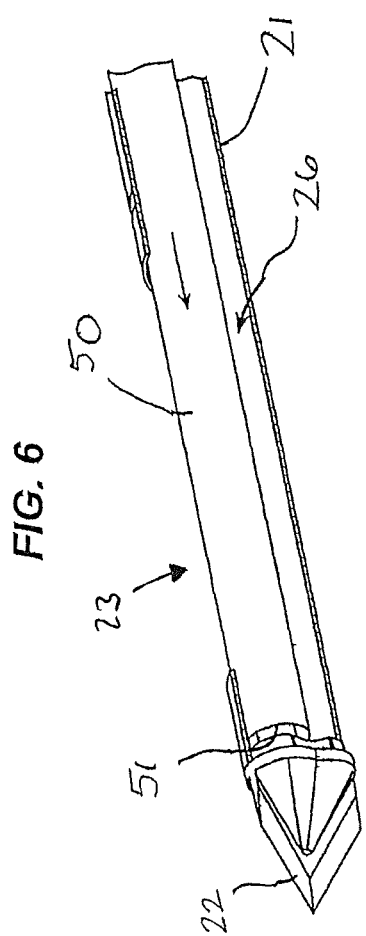
FIG. 6 depicts a fourth series view of part of the needle of the biopsy device of FIG. 1, with the needle shown in cross section and with the cutter in the advanced, distal position.

FIG. 5 depicts cutter (50) fully retracted by cutter actuator (110), such that lateral aperture (23) is completely unobstructed by cutter (50). In this configuration tissue can prolapse through lateral aperture (23) within first lumen (25) under the force of gravity, due to internal pressure of the tissue (e.g., caused by displacement of the tissue upon insertion of needle (20), etc.), and/or with vacuum provided through second lumen (26) and transmitted through openings (28) and/or by vacuum provided through cutter lumen (52). FIG. 6 depicts cutter (50) after it has been advanced to close off lateral aperture (23) once tissue has been captured within first lumen (25) (shown best in FIG. 5). With the tissue severed, it is captured within cutter lumen (52) and ready for proximal transport to tissue sample holder (40). Such proximal transport of tissue through cutter lumen (52) to reach tissue sample holder (40) may be provided by drawing a vacuum through the proximal portion of cutter lumen (52) (e.g., behind the captured tissue sample) while venting a distal portion of cutter lumen (52) (e.g., in front of the captured tissue sample) to provide a pressure differential. Alternatively, tissue samples severed by cutter (50) may be communicated proximally to tissue sample holder (40) or be otherwise dealt with in any other suitable fashion.

B. Exemplary Marker Delivery Device

Figure 7:
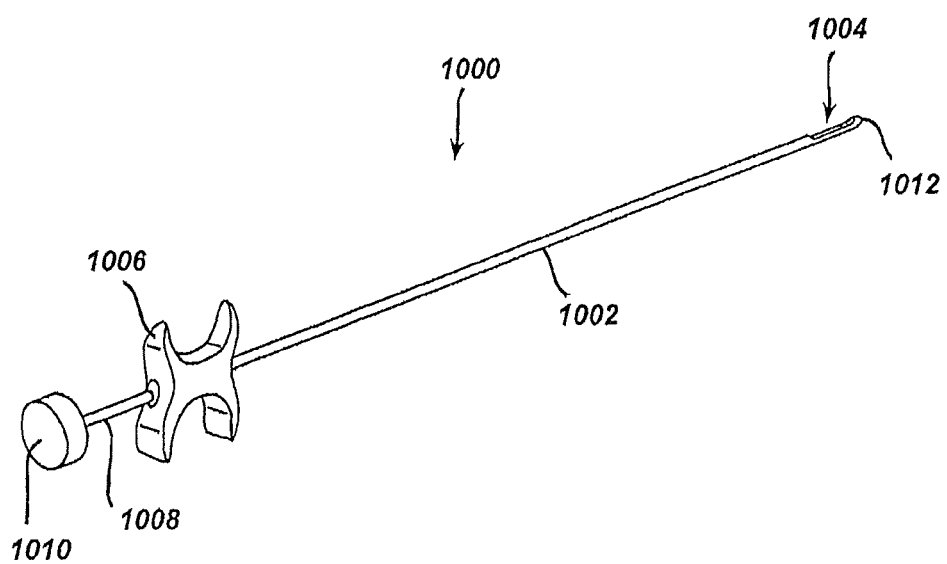
FIG. 7 depicts a perspective view of an exemplary marker delivery device.
Figure 8:
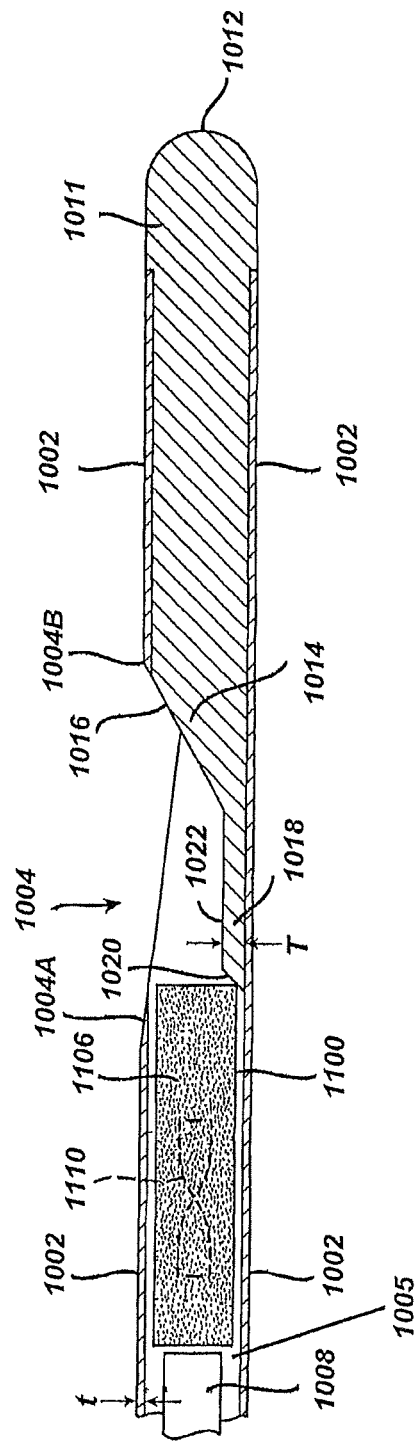
FIG. 8 depicts a cross-sectional view of a distal portion of the marker delivery device of FIG. 7.
Figure 9:
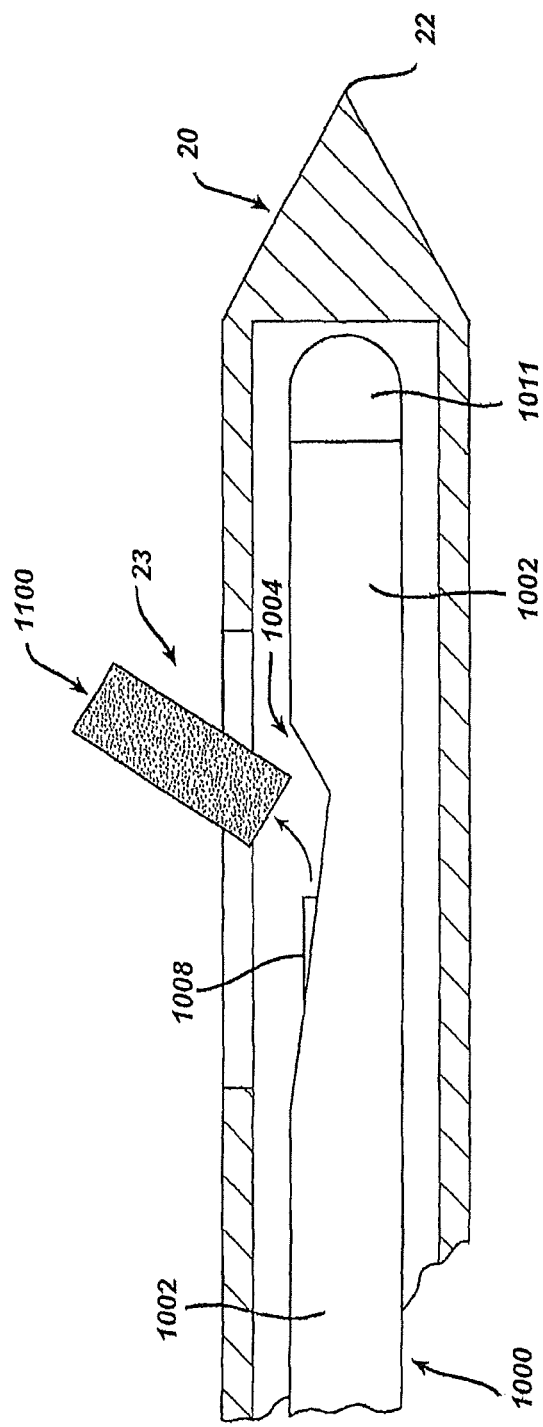
FIG. 9 depicts a side view the marker delivery device of FIG. 7 inserted in a biopsy device needle, with the biopsy device needle shown in cross-section, and with a marker being deployed through aligned lateral openings of the marker delivery device and the biopsy device needle.

After obtaining a tissue sample, in some settings, it may be desirable to mark the location of the biopsy site for future reference. For instance, one or more markers may be deposited at a biopsy site after a tissue sample is taken from the biopsy site. Of course one or more markers may be deposited at a biopsy site before or during the sample taking procedure as well. FIGS. 7-9 illustrate an exemplary marker delivery device (1000), which includes an elongate flexible outer deployer tube (1002) a side opening (1004) formed near to, but spaced proximally from, the distal end of the deployer tube (1002). A grip (1006) is provided at the proximal end of deployer tube (1002). A push rod (1008) extends coaxially in deployer tube (1002) such that push rod (1008) is configured to translate within deployer tube (1002) to displace one or more markers (1100) through the side opening (1004) as shown in FIG. 9. Deployer tube (1002) and rod (1008) may be relatively flexible in bending so that the deployer tube (1002) may be inserted along a straight or curved path to deploy a marker (1100) at a biopsy site. A plunger (1010) is provided at the proximal end of rod (1008) for pushing rod (1008) distally in deployer tube (1002) to deploy a marker (1100) out of the deployer tube (1002). A user may grasp grip (1006) with two fingers, and may push on plunger (1010) using the thumb on the same hand, so that marker delivery device (1000) may be operated by a user's single hand. A spring (not shown) or other feature may be provided about rod (1008) to bias rod (1008) proximally relative to grip (1006) and deployer tube (1002).

FIG. 8 depicts a cross-sectional view of a distal portion of marker delivery device (1000). FIG. 8 shows a biopsy marker (1100) disposed in the internal lumen (1005) of deployer tube (1002). Marker (1100) of the present example comprises a biodegradable or otherwise bioresorbable body (1106), such as a generally cylindrically shaped body of collagen or other suitable polymeric material, and a metallic, generally radiopaque marker element (1110) (shown in phantom) disposed within or otherwise carried by the body (1106). Marker (1100) may be composed and/or configured in accordance with the teachings of any of the various U.S. Patents, U.S. Patent Application Publications, or U.S. Patent Applications cited herein. Alternatively, marker (1100) may have any other suitable composition and/or configuration. It should also be understood that a plurality of markers (1100) may be provided within deployer tube (1002) (e.g., in an end-to-end arrangement, etc.), if desired. If a plurality of markers (1100) are used, it should be understood that a plurality of markers (1100) within a single deployer tube (1002) may have the same size, shape, and/or composition. Alternatively, a plurality of markers (1100) within a single deployer tube (1002) may have different sizes, shapes, and/or compositions.

Deployer tube (1002) may be formed of any suitable metallic or non-metallic material, or even a combination of metallic and non-metallic materials. In the present example, deployer tube (1002) is formed of a relatively flexible, thin walled hollow tube formed of a suitable medical grade plastic or polymer. One suitable material is a thermoplastic elastomer, such as Polyether block amide (PEBA), such as is known under the tradename PEBAX. Deployer tube (1002) may thus be formed of PEBAX, and may be substantially transparent to visible light and X-ray. Side opening (1004) may be formed by cutting away a portion of the wall of deployer tube (1002); or using any other suitable technique. Side opening (1004) communicates with an internal lumen (1005) of deployer tube (1002). Side opening (1004) extends axially (in a direction parallel to the axis of lumen (1005)) from a proximal opening end (1004A) to a distal opening end (1004B), as illustrated in FIG. 8.

The distal tip (1012) extending from the distal end of deployer tube (1002) may be rounded as shown in FIG. 8. Of course, distal tip (1012) may alternatively have any other suitable configuration. Still referring to FIG. 8, marker delivery device (1000) of the present example has the distal end of deployer tube (1002) closed by a unitary endpiece (1011) formed in place in the distal end of deployer tube (1002), with a part of endpiece (1011) extending into internal lumen (1005) of deployer tube (1002). Distal endpiece (1011) may be a molded or cast component, and may provide an integrally formed combination of tip (1012), a ramp (1014) having a ramp surface (1016), and a marker engaging element (1018). Ramp surface (1016) may aid in directing marker (1100) from internal lumen (1005) through side opening (1004). Marker engaging element (1018) may be employed to substantially retain marker (1100) in internal lumen (1005) until the user intends to deploy marker (1100).

Marker engaging element (1018) of the present example is disposed within internal lumen (1005), and at least a portion of marker engaging element (1018) is disposed distally of proximal end (1004A) of side opening (1004). Marker engaging element (1018) extends along a portion of the floor of lumen (1005) under the opening (1004); and is positioned to reinforce the portion of deployer tube (1002) in which opening (1004) is formed. For instance, by positioning marker engaging element (1018) underneath opening (1004) as shown in FIG. 8, marker engaging element (1018) may help to substantially stiffen deployer tube (1002) in the region where the wall of deployer tube (1002) is cut to form opening (1004). Marker engaging element (1018) extends from the proximal-most portion of ramp surface (1016), and does not extend proximally of side opening (1004), though in some other versions, a portion of marker engaging element (1018) could extend proximally of opening (1004) if desired. Marker engaging element (1018) is in the form of a step having a generally uniform thickness (T) along the element's axial length, except that marker engaging element (1018) has a tapered proximal end (1020) in the present example. Tapered proximal end (1020) may form an included angle with the longitudinal axis of the lumen (1005) (included angle with a horizontal line in FIG. 8) of about 45 degrees, while ramp surface (1016) may form an included angle with the longitudinal axis of about 30 degrees. Of course, these angles are mere examples, and it should be understood that any other suitable angles may be used. As shown in FIG. 8, an upwardly facing surface (1022) (surface facing opening (1004)) of marker engaging element (1018) extends distally from tapered proximal end (1020) of marker engaging element (1018) to contact ramp surface (1016).

The thickness (T) of marker engaging element (1018) may be greater than the wall thickness (t) of deployer tube (1002). For instance, in some versions, thickness (T) is at least about twice the thickness (t). By way of example only, the thickness (T) of marker engaging element (1018) may be between about 0.018 inch to about 0.040 inch; and the wall thickness (t) of deployer tube (1002) may be between about 0.005 inch to about 0.008 inch. The internal diameter of lumen (1005) may be about 0.120 inch. Of course, any other suitable dimensions may be used for these components. It should be understood that, as with other components described herein, marker engaging element (1018) may have any other suitable configuration, and may even be omitted as desired.

If desired, the marker engaging element (1018), ramp (1014), and/or tip (1012) may be formed of, or include, a material that is relatively more radiopaque than the wall of deployer tube (1002). For instance, where marker engaging element (1018), ramp (1014), and tip (1012) are formed as an integral endpiece (1011), endpiece (1011) may include a radiopaque additive, such as barium sulfate. By way of example only, endpiece (1011) may be a component molded of PEBAX, with about 20 percent by weight barium sulfate added to the molten PEBAX mold composition. The relatively more radiopaque marker engaging element (1018), ramp (1014), and tip (1012) may be useful in distinguishing the position of those components using radiographic imaging. Also, where ramp (1014) and/or step of marker engaging element (1018) is/are positioned in association with opening (1004), the addition of a radiopaque material may help identify the position of opening (1004), and the position of the marker (1100) relative to opening (1004), before, during, or after deployment of marker (1100).

In some versions, deployer tube (1002) is generally transparent to visible light and x-ray; while endpiece (1011) is generally opaque to visible light and x-ray. If desired, endpiece (1011) may be colored with a dye or other suitable colorant in a liquid mold composition. For example, it may be desirable to have different size markers (e.g. length and/or diameter, etc.) for different biopsy procedures. For instance, it may be desirable to provide a larger marker if a relatively large biopsy sample is taken; and a smaller marker if a relatively small biopsy sample is taken. Endpiece (1011) may be colored using one of multiple colors to indicate the size of the marker disposed in deployer tube (1002). For instance, if three marker sizes are provided, endpiece (1011) may be colored one of three colors to identify which of the marker sizes are disposed in the particular marker delivery device (1000). Endpiece (1011) may also be colored to indicate a particular size (e.g., diameter or length, etc.) or type of biopsy needle with which the marker delivery device (1000) is to be used. Additionally, multiple marker delivery devices (1000) may be packaged in kit form, with the kit including marker delivery devices (1000) having different size markers and correspondingly colored endpieces (1011). Still other variations will be apparent to those of ordinary skill in the art in view of the teachings herein.

As shown in FIG. 9, marker delivery device (1000) may be used to deploy a marker (1100) to mark a particular location within a patient. For instance, FIG. 9 depicts marker delivery device (1000) being used through a biopsy needle (20). In particular, FIG. 9 shows the distal end of marker delivery device (1000) disposed within the interior of needle (20). Needle (20) of this example has a closed distal end with a piercing tip (22); and a lateral tissue receiving aperture (23). It should be understood that needle (20) may be positioned in tissue, and a biopsy sample may be obtained through lateral aperture (23), thereby providing a biopsy cavity adjacent lateral aperture (23). Then, after the tissue sample has been obtained and transferred proximally through needle (20), and without removing needle (20) from the patient's tissue, marker delivery device (1000) may be inserted through a proximal opening (not shown) in needle (20) described later herein. In particular, needle (20) and marker delivery device (1000) are positioned such that opening (1004) of deployer tube (1002) and lateral aperture (23) of needle (20) are substantially aligned axially and circumferentially. Then, with marker delivery device (1000) and needle (20) so positioned at the biopsy cavity, push rod (1008) may be advanced to deploy marker (1100) up ramp surface (1016), through opening (1004), and then through lateral aperture (23), into the biopsy cavity.

Marker delivery device (1000) may thus be introduced to a biopsy site through biopsy needle (20), which can be the same needle (20) used to collect a tissue sample from the biopsy site. Biopsy needle (20) may be of the type used with single insertion, multiple sample vacuum assisted biopsy devices. Several such biopsy devices are disclosed in the various U.S. Patents, U.S. Patent Application Publications, and U.S. Patent Applications that have been referred to and incorporated by reference herein, though it should be understood that marker delivery device (1000) may be used with various other biopsy devices.

It may be desirable in some (but not necessarily all) settings to substantially prevent a marker from unintentionally falling out of a deployer, such as at a time prior to the intended deployment. In addition, it may be desirable in some (but not necessarily all) settings to guide and/or steady the tip of a flexible tube of a deployer as the tip is inserted into a biopsy device or other access device used to provide a path to a biopsy site. Some of these and other modifications and alternative configurations of a marker delivery device are described in U.S. Pub. No. 2011/0071423, entitled "Flexible Biopsy Marker Delivery Device," published Mar.

24, 2011, the disclosure of which is incorporated by reference herein; and U.S. Non-Provisional patent application Ser. No. 12/787,492, entitled "Biopsy Marker Delivery Device," filed May 26, 2010, the disclosure of which is incorporated by reference herein.

While the above paragraphs provide an enabling description of an exemplary biopsy device (10) and marker delivery device (1000) and their use, further description as well as exemplary methods of operation for an exemplary biopsy device (10) are provided with the teachings of U.S. Non-Provisional patent application Ser. No. 12/709,624, entitled "Spring Loaded Biopsy Device," filed Feb. 22, 2010, and U.S. Pub. No. 2008/0214955, entitled "Presentation of Biopsy Sample by Biopsy Device," published Sep. 4, 2008, the disclosures of which are incorporated by reference herein. Further descriptions as well as exemplary methods of operation for an exemplary marker delivery device (1000) are provided with the teachings of U.S. Pub. No. 2011/0071423, entitled "Flexible Biopsy Marker Delivery Device," published Mar. 24, 2011, the disclosure of which is incorporated by reference herein; U.S. Non-Provisional patent application Ser. No. 12/787,492, entitled "Biopsy Marker Delivery Device," filed May 26, 2010, the disclosure of which is incorporated by reference herein; and U.S. patent application Ser. No. 13/205,189, entitled "Access Chamber and Markers for Biopsy Device," filed Aug. 8, 2011, the disclosure of which is incorporated by reference herein. Of course, the above examples of construction and use of biopsy device (10) and marker delivery device (1000) are merely illustrative. Other suitable ways in which biopsy device (10) and marker delivery device (1000) may be made and used will be apparent to those of ordinary skill in the art in view of the teachings herein.

II. Exemplary Tissue Sample Holder with Removable Tray

FIGS. 10-13 show an exemplary tissue sample cap (41) and tray (46). Tissue sample cap (41) and tray (46) of the present example are components of tissue sample holder (40) described above. For instance, cap (41) shown in FIGS. 10-13 is operable with cup (42) as shown in FIG. 1 and described above. As discussed, latches (43) of cap (41) cooperate with features of cup (42) to removably secure cap (41) to cup (42). As discussed below in greater detail, latches (43) of cap (41) cooperate with features of tray (46) to disengage tray (46) from cap (41).

Figure 10:
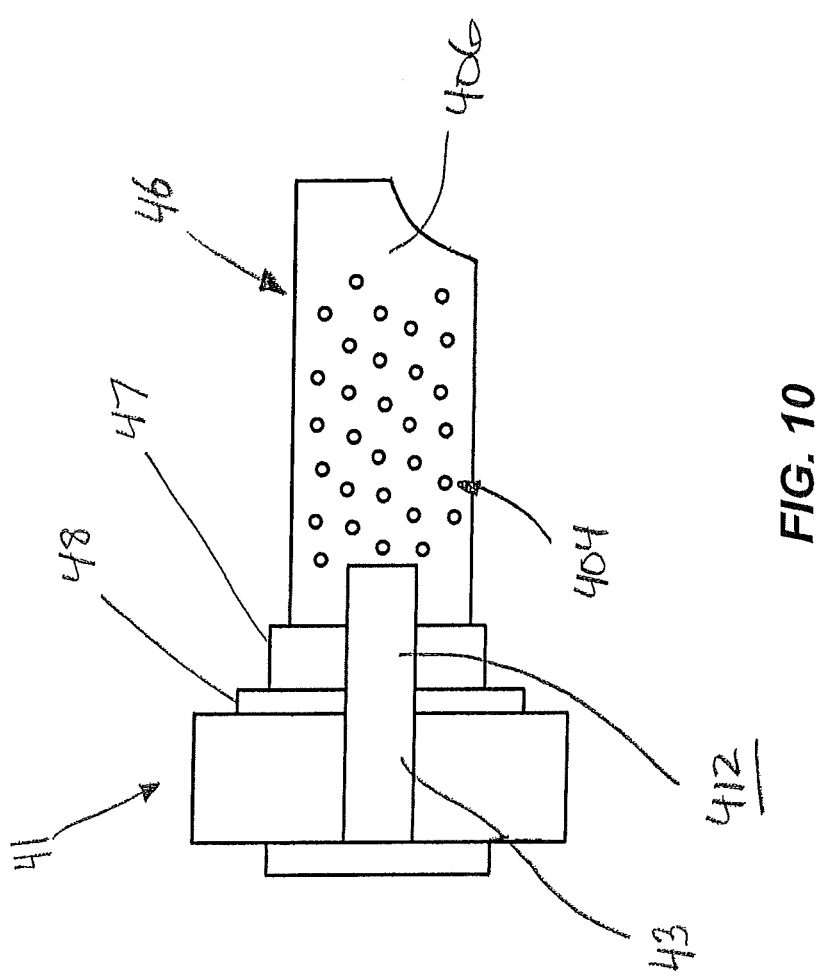
FIG. 10 depicts a side view of an exemplary tray and cap of a tissue sample holder.
Figure 11:
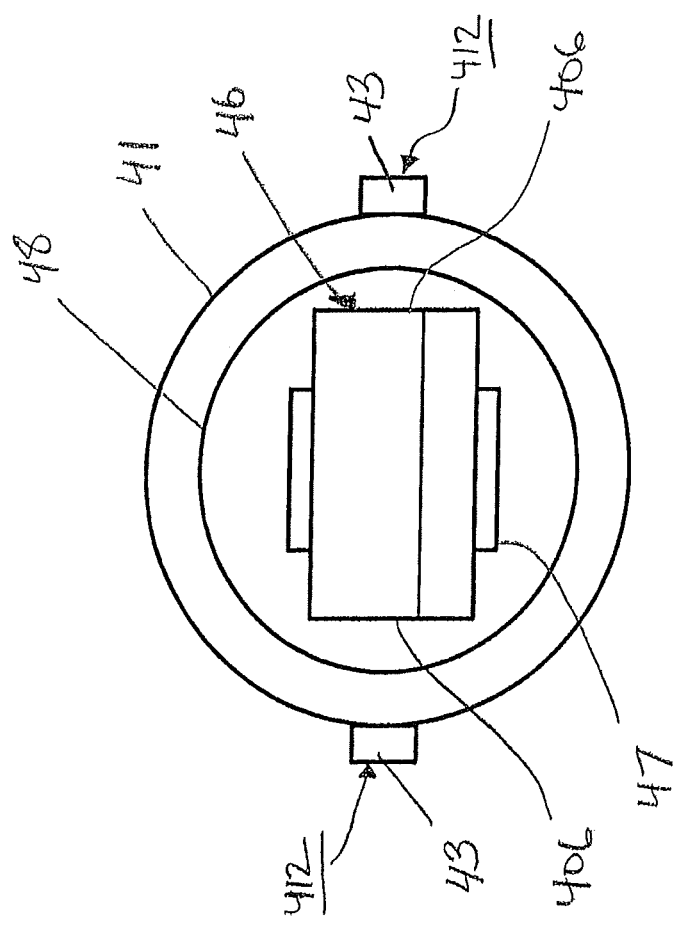
FIG. 11 depicts a front view of the tray and cap of FIG. 10, shown from the tray end.

As shown in FIG. 10, tray (46) is integral with cap (41). Thus, when cap (41) is removed from cup (42), both cap (41) and attached tray (46) are removed from cup (42) as a single unit. In some versions, tray (46) is removably secured to cap (41), such that tray (46) may be separated from cap (41). In the present example, tray (46) is removably secured to cap (41) by an interference fitting or snap fitting. For example, tray (46) includes proximal end (47), which has a generally rectangular shape in the present example, although other shapes could be used as well. Proximal end (47) is configured such that it engages with an interior receiving member (48) of cap (41). Interior receiving member (48) is configured such that it includes a docking member (not shown) to which proximal end (47) fits snugly against so as to create an interference fitting between the two. In some versions, an o-ring (not shown) or elastomeric material may be included on the docking member (not shown) and/or proximal end (47) for creating a frictionally secure and sealed connection between tray (46) and cap (41). While the above described interference fitting is one way to securely, yet removably, attached tray (46) to cap (41), other suitable ways in which to connect tray (46) to cap (41) will be apparent to those of ordinary skill in the art based on the teachings herein.

Figure 12:
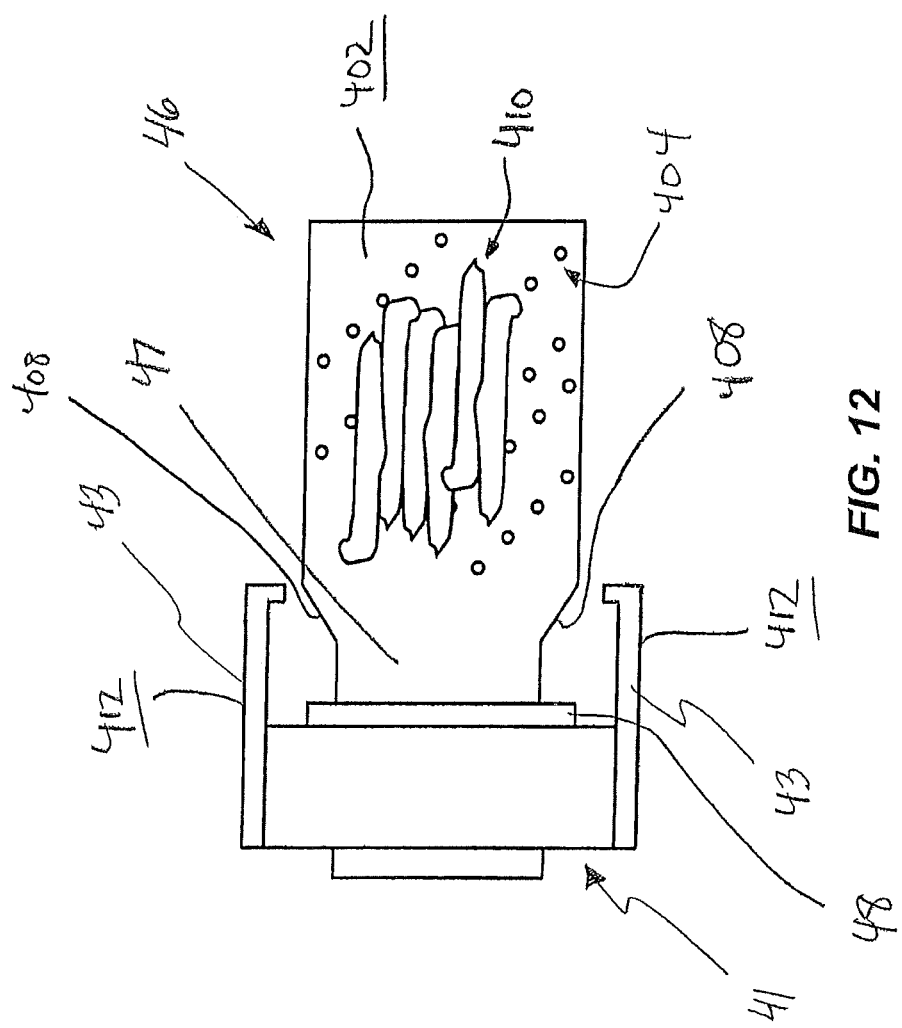
FIG. 12 depicts a top view of the tray and cap of FIG. 10, shown with the tray and cap removed from an outer cup, but with tray attached to cap.
Figure 13:
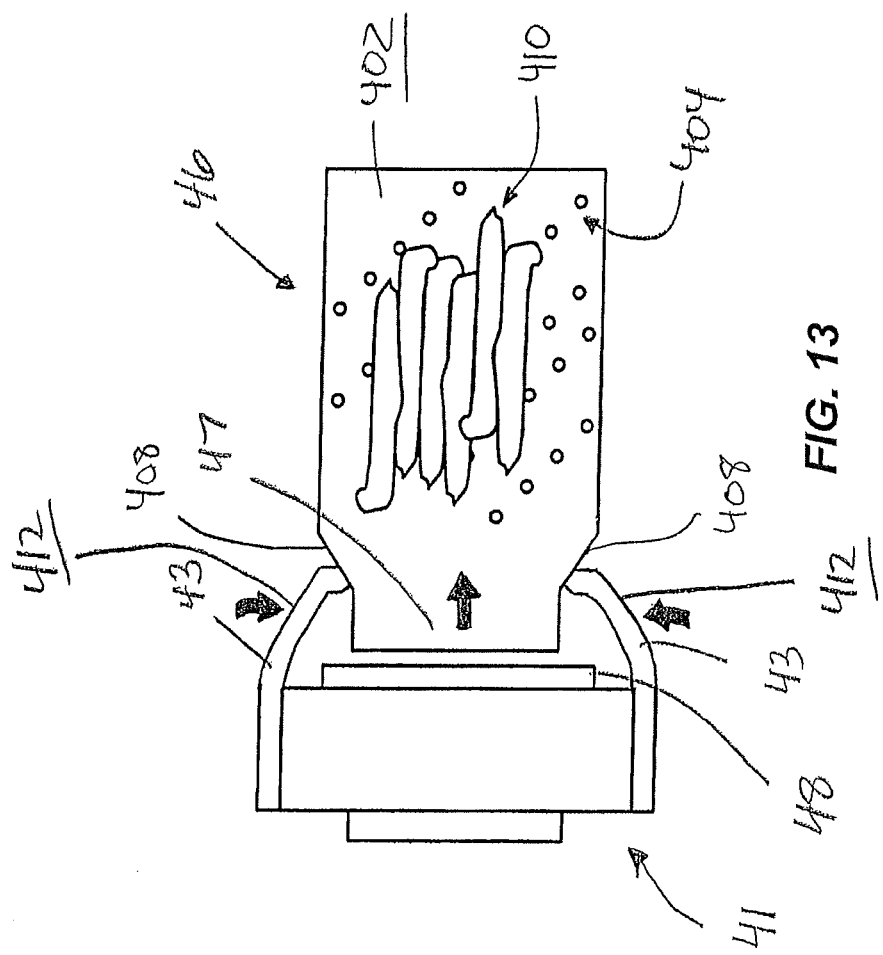
FIG. 13 depicts a top view of the tray and cap of FIG. 10, shown with the tray ejected from the cap.

Tray (46) of the present example comprises sample surface (402) and openings (404). As shown in FIGS. 12-13, sample surface (402) is configured to receive tissue samples (410) that were severed by cutter in a biopsy procedure. In the present example, tissue samples (410) are transported through the cutter lumen (52) to sample surface (402) by vacuum. Of course other means to deposit tissue samples (410) on sample surface (402) (e.g., pressurized fluid such as air or saline, etc.) will be apparent to those of ordinary skill in the art based on the teachings herein. Also as shown in FIGS. 10-13, sample surface (402) comprises upright side portions (406) and inclined faces (408). Inclined faces (408) couple sample surface (402) and upright side portion (406) with proximal end (47) of tray (46). Openings (404) of tray (46) are positioned along upright side portions (406) of tray (46) and along sample surface (402). Of course, openings (404) may alternatively have any other suitable arrangement that will be apparent to those of ordinary skill in the art based on the teachings herein; or openings (404) may be eliminated entirely. In the present example, openings (404) are large enough to permit fluid that is transported to tray (46) (e.g., by vacuum along with the tissue samples, or by vacuum as part of a drainage procedure, etc.) to flow through tray (46) and be collected by another structure (e.g., in the present example the fluid passing through openings (404) is retained within cup (42); yet are small enough such that tissue samples (410) are retained on sample surface (402)).

Tray (46) of the present example is constructed from a transparent plastic. Of course other materials, including non-transparent materials, may be used in other versions as will be appreciated by those of ordinary skill in the art based on the teachings herein. In some versions, tray (46) includes a ceiling member (not shown) that connects to upright side portions (406) and thus extends above and over sample surface (402). In some such versions, all of tray (46) or portions of tray (46) are constructed from a transparent plastic. Having a tray (46) with all or a portion constructed from transparent materials may permit a user to visualize the collected tissue samples (410) once cap (41) and tray (46) have been removed from cup (42). Of course, in some other versions, all or portions of cup (42) may also be made from transparent materials such that collected tissue samples (410) can be visualized even when cap (41) is still connected with cup (42), tray (46) being located within cup (42).

As shown by comparing FIGS. 12 and 13, another feature of the present cap (41) and tray (46) combination is the ability to eject tray (46) from cap (41). With an ejectable tray (46), the entire tray (46) including any tissue samples (410) captured on sample surface (402) can may be ejected from cap (41) into a container of formalin or some other fluid. In the present example, latches (43) have resilient properties. When latches (43) are pushed from outer sides (412) toward a central axis of tray (46), latches (43) flex inward and contact inclined faces (408) of tray (46). With the shape of inclined faces (408), as latches (43) are depressed further when contacting inclined faces (408), tray (46) is driven in a distal direction away from cap (41). This force and driving motion are sufficient so proximal end (47) separates from docking member (not shown) of cap (41), thereby effectively ejecting tray (46) from cap (41).

In an exemplary use, after conducting a biopsy procedure and collecting tissue samples (410) on sample surface (402) of tray (46), a user twists cap (41) to disengage latches (43) from lip (44) of outer cup (42). With latches (43) disengaged from lip (44), cap (41) and the attached tray (46) are removed from outer cup (42). A user now visualizes the captured tissue samples (410). When ready to place the tissue samples (410) into a container of formalin or other fluid, a user aligns tray (46) with the opening in the container of formalin and then ejects tray (46) by depressing latches (43) inward toward a central axis of cap (41) and tray (46). The ejection force provided by latches (43) is sufficient to overcome the interference fitting between proximal end (47) of tray (46) and docking member (not shown) of cap (41), thereby depositing tray (46) with tissue samples (410) into the container of formalin or other fluid. At this point, the container of formalin with the samples can be sealed and transported for testing. Further, if desired by a user, another tray (46) may be installed on cap (41) for a subsequent procedure or to capture additional tissue samples (410).

It should be understood from the foregoing that, in the present example, a user may remove cap (41) from outer cup (42), visualize tissue samples (410), and eject tray (46) from cap (41) without having to reposition the user's hand on cap (41). For instance, a user may grasp cap (41) along outer sides (412) of latches (43) and can then rotate cap (41) to disengage cap (41) from outer cup (42), followed by depressing latches (43) to eject tray (46). Of course, this one-handed action is not required, and in this and other versions repositioning of the user's hand may occur if desired or if necessary. In addition, in the present example, the operability of latches (43) is such that when cap (41) is engaged with outer cup (42), latches (43) cannot be sufficiently depressed to eject tray (46). This is the case because outer cup (42) prevents latches (43) from being able to flex inward and contact inclined faces (408) of tray (46) as described above.

While the above paragraphs describe an exemplary sample holder (40) having a removable tray (46) that is ejected by depressing latches (43), other ways in which to selectively detach tray (46) from cap (41) will be apparent to those of ordinary skill in the art based on the teachings herein. By way of example only, cap (41) and tray (46) may be adapted with various spring and trigger components where tray (46) may be spring loaded to cap (41) and the trigger may be selectively actuated to release the spring and thereby eject tray (46). Thus, it should be understood that interaction between resilient latches (43) and inclined faces (408) is just one merely illustrative example.

III. Exemplary Tissue Sample Holder with Threaded Cap

FIGS. 14-16 show exemplary components of a biopsy device that include outer cup (42), threaded cap (241), and threaded sample container (300). Outer cup (42) of the present example is as described previously, including lip (44) and gaps (45) for selective engagement with latches (243) of cap (241). Engagement of latches (243) is as described above with respect to outer cup (42) and latches (43) of cap (41). In addition to latches (243), cap (241) includes internal threads (202). Threads (202) are configured to engage with complementary threads (302) of sample container (300). While sample containers (300) may come in a variety of sizes, it will be apparent to those of ordinary skill in the art based on the teachings herein that caps (241) may be adapted to function with a variety of sample containers (300), including but not limited to conventional sample containers.

In an exemplary use, after conducting a biopsy procedure and collecting tissue samples, a user twists cap (241) to disengage latches (243) from lip (44) of outer cup (42). With latches (243) disengaged from lip (44), cap (241) is removed from outer cup (42). A user now visualizes the captured tissue samples. In the present example, the tissue samples are captured and contained within the space defined by outer cup (42). As discussed above, tissue samples may instead be collected on a tray (e.g., tray (46)), or within a rotatable serial tissue sample capturing structure as described previously, or by any other suitable means. Based on the teachings herein, suitable ways to modify the exemplary configuration shown in FIGS. 14-16 to incorporate a tray or other tissue collection structure will be apparent to those of ordinary skill in the art. It should also be understood that, in some versions (e.g., those in which liquid is evacuated from cup (42) at the end of a biopsy procedure, etc.), the entire biopsy device (10) may be oriented vertically, with tip (22) pointing upward, such that tissue samples are essentially dumped onto the inner surface of cap (241) before cap (241) is removed from cup (42), and such that tissue samples may be transported to sample container (300) on the inner surface of cap (241).

After visualizing the tissue samples, a user then places the tissue samples into sample container (300). In the present example, a user simply empties the contents of outer cup (42) into sample container (300), such as by tilting biopsy device (10) with cap (241) removed to essentially dump the tissue samples from cup (42) into container (300). In some versions, a user filters the contents of outer cup (42) such that only the tissue samples are emptied into sample container (300). In some other versions incorporating a tray (46), the tray (46) containing the tissue samples may be ejected into the sample container (300) as discussed above. Based on the teachings herein, other modes of transferring the tissue samples from the tissue sample holder (40) to sample container (300) will be apparent to those of ordinary skill in the art. In the present example, sample container (300) is a formalin cup used to retain captured biopsy specimens for subsequent analysis of the specimens. Of course other types of containers for sample container (300) will be apparent to those of ordinary skill in the art based on the teachings herein.

With the tissue samples deposited within sample container (300), cap (241) is threadably engaged to the complementary threads of sample container (300). In the present example, latches (243) are configured such that they do not interfere with threadably engaging cap (241) to sample container (300). In some other versions, latches (243) are resilient and act as clamping members on outer surface (304) of sample container (300) in addition, or in the alternative, to the threaded connection. While the above paragraphs describe an exemplary tissue sample holder (40) having a removable cap (241) that threadably engages a sample container (300), other ways in which to engage a cap (241) to a sample container (300) will be apparent to those of ordinary skill in the art based on the teachings herein. By way of example only, cap (241) and sample container (300) may be adapted to engage one another using a similar engagement system as that of cap (241) to outer cup (42). In other words, sample container (300) may have features configured to engage latches (243) that are similar to lip (44) and gaps (45) of cup (42), etc.

IV. Exemplary Tissue Sample Holder Fluid Management Port

FIGS. 17-18 show an exemplary cap (541) for a tissue sample holder such as tissue sample holder (40) described above. Cap (541) of this example is operably configured to selectively connect with an outer cup (not shown) of a tissue sample holder. In some versions outer cup (not shown) is similar to outer cup (42) as described above. In some such versions, cap (541) may include latches similar to latches

(43) described above. However, in the present example, cap (541) threadably connects with outer cup without engaging latches.

Cap (541) comprises port (502) on the distal surface (504) of cap (541), and a seal (506). Seal (506) is operable with port (502) and is generally configured to maintain fluid within the outer cup of the tissue sample holder (e.g., when no other device is otherwise connected with port (502)). However, port (502) is configured such that a syringe (508) is connectable with port (502) to manage fluid within the outer cup. While the present example illustrates and describes syringe (508) as connectable to port (502), other devices suitable to connect to port (502) will be apparent to those of ordinary skill in the art based on the teachings herein. For instance, an auxiliary or additional vacuum may be coupled to port (502) to provide additional vacuum to pull the tissue into the tissue sample holder, such as in accordance with the teachings of U.S. patent application Ser. No. 12/709,695, entitled "Biopsy Device with Auxiliary Vacuum Source," filed Feb. 22, 2010, the disclosure of which is incorporated by reference herein, or otherwise. Alternatively, in a system where the outer cup acts as a collection reservoir for fluid from the biopsy procedure, when a quantity of fluid has been captured within the outer cup that would otherwise require removing the cap or outer cup to empty the outer cup, a user can instead connect syringe (508) (e.g., a 20 cc syringe, etc.) to port (502) and withdraw excess fluid from within the outer cup. Once the user has withdrawn the desired amount of fluid, syringe (508) may be disengaged from port (502) and the seal (506) retains any left-over fluid or subsequently captured fluid within the outer cup. Seal (506) also substantially maintains a vacuum within the cup of the tissue sample holder. It should be understood that syringe (508) may be used to remove liquid from the tissue sample holder one or more times during a biopsy procedure, even while the needle of the biopsy device is still inserted in a patient (e.g., in a patient's breast, etc.).

In the present example, seal (506) comprises a self-sealing membrane. As shown in FIG. 18, seal (506) is positioned along the interior wall (510) of cap (541). In use, when syringe (508) is attached to port (502), seal (506) is punctured to allow fluid to be passed between the outer cup and syringe (508). Once syringe (508) is detached from port (502), the properties of the membrane seal the puncture thereby restoring the integrity of seal (506). As another merely illustrative example, seal (506) may be part of a valve that is actuated to open upon coupling of syringe (508) with port (502). It should also be understood that port (502) may include a luer lock feature to assist in removably securing syringe (508) to port (502). Still other suitable structures and configurations for a sealing port (502) positioned on a cap (541) of a tissue sample holder will be apparent to those of ordinary skill in the art in view of the teachings herein. It should also be understood that port (502) may include a screen and/or other type of feature configured to substantially prevent tissue samples or tissue particles from clogging port (502) as liquid is removed from port (502).

V. Exemplary Tissue Sample Holder with Integrated Marker Delivery Access

FIGS. 19-22 show an exemplary cap (641) and tray (646) of a tissue sample holder (40) incorporating integrated access for marker delivery device (1000). In the present example, cap (641) comprises a body (601) with a port (602) on a proximal surface (604) of cap (641). Cap (641) further comprises seal (606), which in the present example is positioned within body (601). In some versions, seal (606) comprises an integrated zero closure seal. By way of example only, seal (606) may comprise a twisted diaphragm similar to the seal disclosed in U.S. Pub. No. 2008/0146884, entitled "Fully Automated Iris Seal for Hand Assisted Laparoscopic Surgical Procedures," published Jun. 19, 2008, the disclosure of which is incorporated by reference herein. As another merely illustrative example, seal (606) may comprise an iris seal composed of overlapping members similar to the seal disclosed in U.S. Pub. No. 2008/0146882, entitled "Handoscopy Interwoven Layered Seal Laparoscopic Disk," published Jun. 19, 2008, the disclosure of which is incorporated by reference herein. Further still, seal (606) may comprise a proximally-oriented duckbill type seal. Of course, other suitable types of seals will be apparent to those of ordinary skill in the art in view of the teachings herein (e.g., a septum seal, etc.). It should also be understood that seal (606) may comprise a removable stopper, flap, latch, and/or other feature. Port (602) is configured with a funnel shape or frustoconical in the present example, for easily guiding entry of marker delivery device (1000). Furthermore, in the present example, proximal surface (604) of body (601) has a funnel shape or frustoconical shape thereby assisting in guiding marker delivery device (1000) to port (602). Any other suitable configurations may be used.

Port (602) leads to a passage (608), which is at least partially defined by tray (646) and runs along the underside length of tray (646). A hinged ramp (607) is biased downwardly from tray (646) and extends distally and downwardly from the top of an arcuate section (616) toward a sample surface (612) of tray (646) such that when tissue samples are transported proximally through cutter lumen (52), hinged ramp (607) diverts the tissue samples into tray (646). Seal (606) separates port (602) and passage (608) such that seal (606) must be opened or penetrated by marker delivery device (1000) for marker delivery device (1000) to enter passage (608). Passage (608) ultimately, directly or indirectly through other structures, leads to needle (20) such that a side opening (1004) of deployer tube (1002) of marker delivery device (1000) can be aligned with lateral aperture (23) of needle (20). For instance, in the example shown in FIGS. 19-22, when marker delivery device (1000) is inserted, marker delivery device (1000) urges ramp (607) upwardly to allow marker delivery device (1000) to continue along the axial length of passage (608) into lumen (52) of cutter (50) and toward needle (20). With this arrangement, a marker (1100) may be deployed at a biopsy site as described in greater detail above. By way of example only, passage (608) may align with and lead to cutter lumen (52), such that deployer tube (1002) of marker delivery device (1000) may be fed distally through port (602), along passage (608) (and underneath ramp (607)), and through cutter lumen (52), until side opening (1004) is substantially aligned with lateral aperture (23). In some other versions, sample surface (612) without arcuate section (616) is located below passage (608) such that passage (608) is located above sample surface (612) and still leads to cutter lumen (52), as will be described below.

Tray (646) of the present example connects with cap (641) and comprises upright side portions (610), sample surface (612), and openings (614). Upright side portions (610) contain openings (614), which are operably configured for draining fluid from tray (646) as discussed in previous examples. Of course, in some versions, openings (614) may be entirely omitted. Sample surface (612) extends between upright side portions (610) and comprises a hinged ramp (607) and an arcuate section (616), which in part defines passage (608)—specifically a section of the upper portion of passage (608), as best seen in FIG. 20. In still other versions, arcuate section (616) is omitted. For instance, cap (641) and tray (646) may be configured such that port (602) is located at a vertical position that is substantially higher than sample surface (612) yet is coaxially aligned with cutter lumen (52), such that a deployer tube (1002) has a clear path to cutter lumen (52) via port (602) and such that tissue samples gathered on tissue sample surface (612) will not substantially obstruct passage of deployer tube (1002) to cutter lumen (52) via port (602). Still other suitable configurations will be apparent to those of ordinary skill in the art in view of the teachings herein.

In use, severed tissue samples are transported to tray (646) as described above. At any point in the sampling procedure, or even pre-sampling procedure, a marker (1100) can be deployed at a biopsy site or other site as a reference indicator as discussed above. To place a marker (1100), deployer tube (1002) of marker delivery device (1000) is inserted into port (602). As deployer tube (1002) is advanced distally, deployer tube (1002) contacts seal (606). As deployer tube (1002) is advanced further distally, deployer tube (1002) enters passage (608). Passage (608) connects with needle (20) such that continued advancement of deployer tube (1002) places deployer tube (1002) within needle (20). Once side opening (1004) of deployer tube (1002) is aligned with lateral aperture (23) of needle (20), marker (1100) is deployed to a desired site as described in greater detail above. After marker (1100) has been placed, deployer tube (1002) is withdrawn from needle (20) and biopsy sample capture begins or continues as the case may be. It should thus be understood that a marker (1100) may be deployed without having to withdraw needle (20) from the patient and without having to remove cap (641) or any other component of the tissue sample holder from the biopsy device (10). While one approach for integrated access for a marker delivery device (1000) has been discussed above, other approaches and/or modifications for such integrated access will be apparent to those of ordinary skill in the art based on the teachings herein.

The preceding paragraphs have described various exemplary features for a tissue sample holder of a biopsy device. For instance, among others, some of the features include a removable tray (46), a threaded cap (241) configured to threadably engage a sample container (300), a port (502) for withdrawing excess fluid from a tissue sample holder, and integrated access for a marker delivery device (1000). Based on the teachings herein, it will be apparent to those of ordinary skill in the art that features described herein may be combined or interchanged. For example, a removable tray (46) may be adapted for use with a threaded cap (241) such that once tray (46) is ejected into a sample container (300), remaining cap (241) may be attached to sample container (300) by the above described system of complementary threads. Similarly, a cap (41) that is operable to eject a tray (46) may also include a port (602) providing access for a marker delivery device (1000). Still other combinations, interchanges, and variations will be apparent to those of ordinary skill in the art based on the teachings herein.

Figure 23:
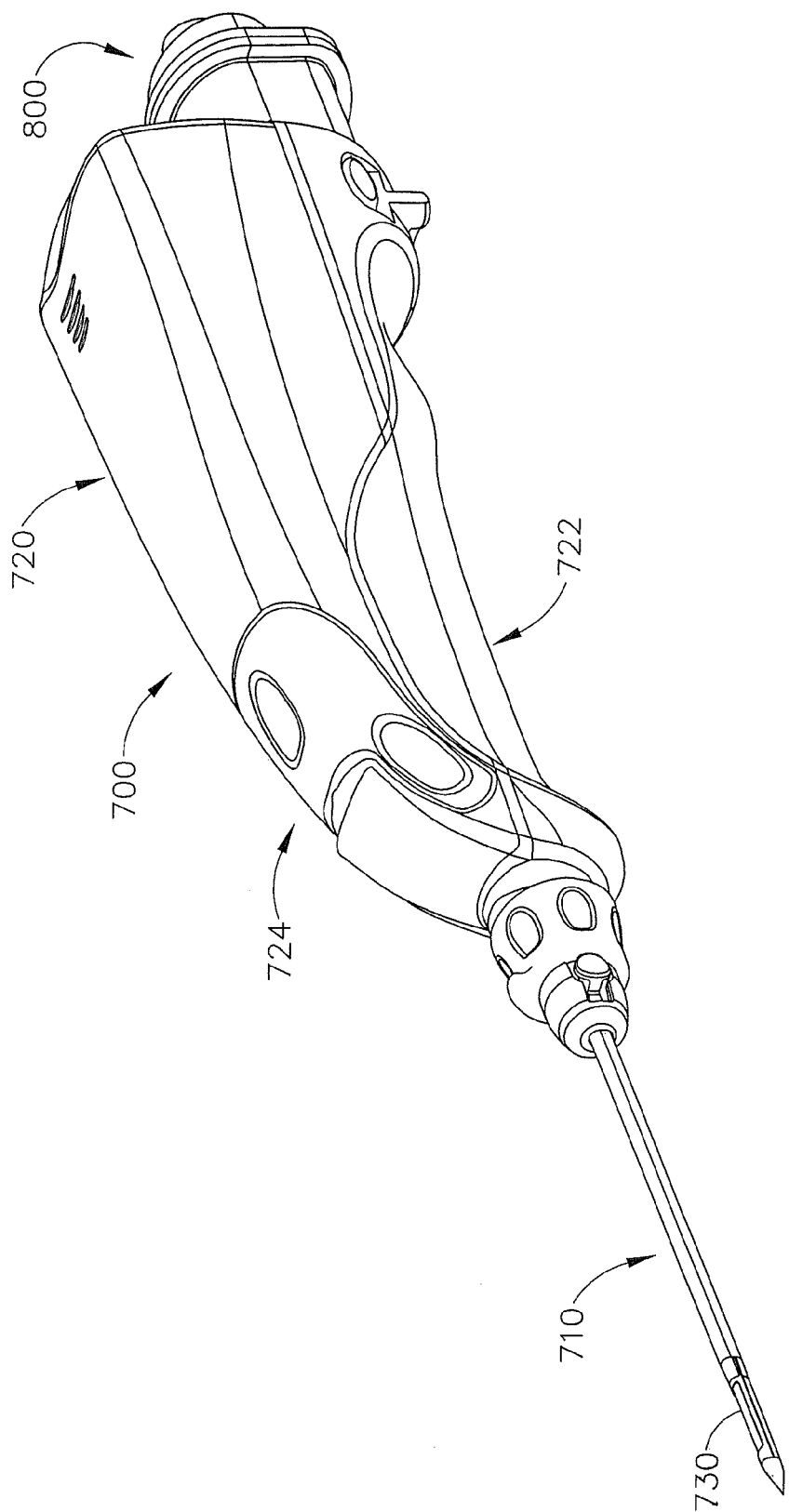
FIG. 23 depicts a perspective view of another exemplary biopsy device.

VI. Additional Exemplary Biopsy Device, Exemplary Recharging Dock, and Exemplary Tissue Sample Holders One exemplary alternative biopsy device (700) is shown in FIG. 23 and comprises a needle (710), a body (720), a tissue sample holder (800), and a cutter (730). Alternative biopsy device (700) may be configured substantially in accordance with biopsy device (10) described previously. In particular, needle (710) extends distally from the distal portion of body (720), while tissue sample holder (800) extends proximally from the proximal portion of body (720). A user may grasp body (720), insert needle (710) into a patient's breast, and collect one or a plurality of tissue samples from within the patient's breast, all with just using a single hand. In some settings, the user may capture a plurality of tissue samples with just a single insertion of needle (710) into the patient's breast. Such tissue samples may be pneumatically deposited in tissue sample holder (800), and later retrieved from tissue sample holder (800) for analysis. While examples described herein often refer to the acquisition of biopsy samples from a patient's breast, it should be understood that biopsy device (700) may be used in a variety of other procedures for a variety of other purposes and in a variety of other parts of a patient's anatomy, including but not limited to a patient's prostate. In the present example, body (720) comprises a probe (722) and a holster (724). Probe (722) and holster (724) are separable components. Needle (710) and tissue sample holder (800) are coupleable to probe (722) while holster (724) houses other internal components, such as those shown in FIG. 2.

Figure 24:
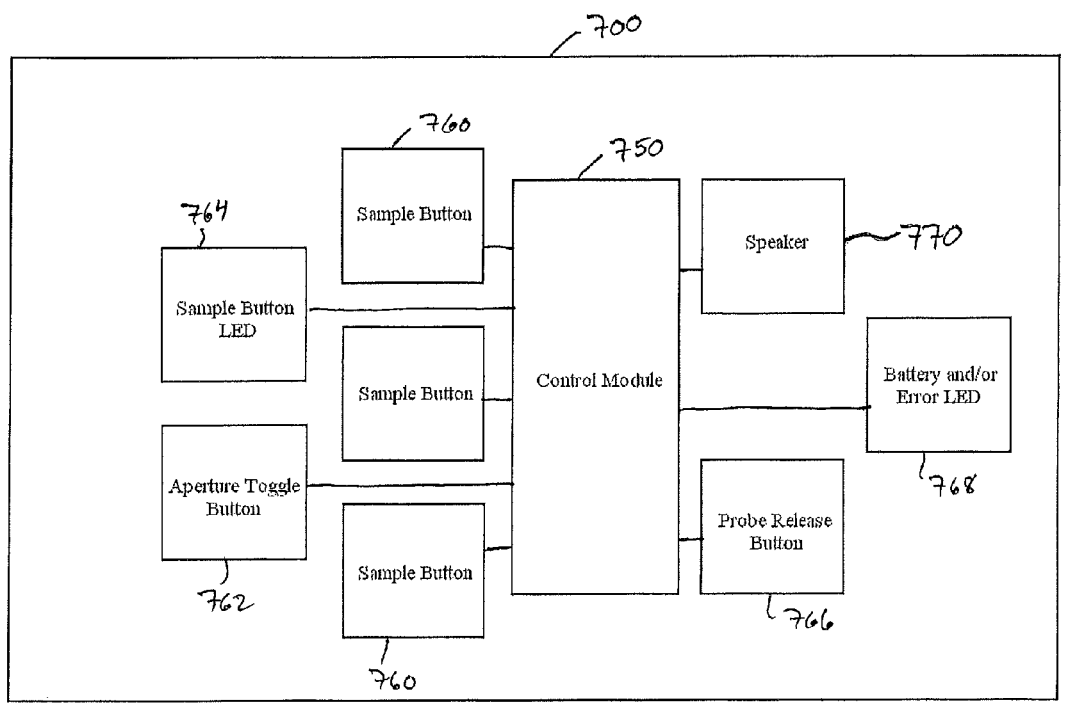
FIG. 24 depicts a block schematic view of various components of the device of FIG. 23.

Merely exemplary components that may be included in or on biopsy device (700) (beyond those shown in FIG. 2) are shown schematically in FIG. 24. In the example shown, biopsy device (700) includes a control module (750). Control module (750) of the present example includes a microcontroller configured to control various aspects of biopsy device (700). In one configuration, control module (750) may be configured to store error data and/or usage data for later analysis. For instance, one or more sample buttons (760) are coupled to control module (750) and activate cutter (730) to sever a tissue sample (such as through the motion of cutter (50) depicted in FIGS. 3-6). Such buttons (760) may be included on holster (724) and/or on probe (722). An aperture toggle button (762) is also coupled to control module (750) and toggles cutter (730) between a position where the lateral aperture is open and a position where the lateral aperture is closed. A sample button LED (764) is coupled to control module (750) and may be configured to indicate whether sampling of tissue is occurring or not. A probe release button (766) may also be coupled to control module (750) to electronically trigger the release of probe (722), though it should be understood that probe release button (766) may alternatively be a mechanical release not coupled to control module (750). Further, one or more LEDs (768) are also coupled to control module (750) and may be configured to indicate whether the power source in holster (724) is out of power and/or some other condition. A speaker (770) is also included and is coupled to control module (750) to provide an auditory indication to a user. Such auditory indications may signal sample taking success, errors, low power, no power, biopsy device-readiness, and/or any other auditory indication. Of course, any or all of these foregoing components may be varied, substituted, supplemented, or omitted from biopsy device (700). While some various components have been described, still other components will be apparent to one of ordinary skill in the art in view of the teachings herein.

A. Exemplary Recharging Dock

Figure 25:
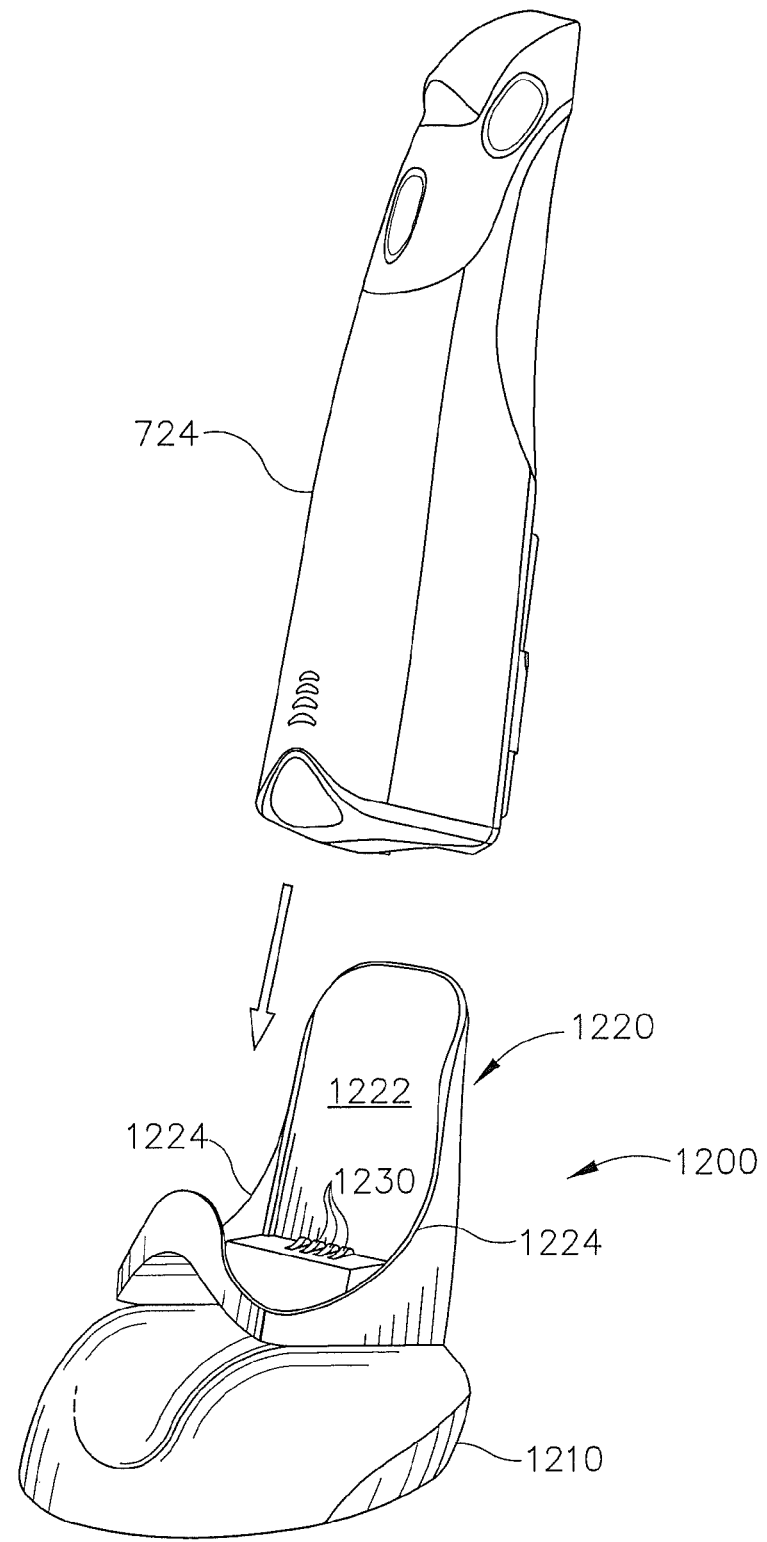
FIG. 25 depicts a perspective view of a holster recharging station for use with the device of FIG. 23.

As noted above, holster (724) is separable from probe (722). In some instances, such as when holster (724) includes an integral power source, such as power source (60) (e.g., one or more lithium ion batteries, etc.), the power source may need to be recharged between uses or between a series of uses of biopsy device (700). In such instances, it may be preferable to include a recharging dock (1200) shown in FIG. 25. Recharging dock (1200) comprises a base (1210), a holster stand (1220), and one or more electrical connectors (1230). Recharging dock (1200) may further include a power cord (not shown) that can be plugged into a wall outlet; or, in some versions, recharging dock (1200) may include a battery within base (1210). Recharging dock (1200) may also further comprise one or more communications ports (not shown), such as a USB port, a serial port, an IEEE (or Firewire) port, an Ethernet port, a telephone jack, a Bluetooth transmitter, a wifi device, a WLAN connection, a 3G or 4G connection, and/or any other suitable communicative device or port. When inserted into holster stand (1220), holster (724) tilts against holster stand (1220) and is held in place by back wall (1222) and sidewalls (1224), such that holster stand (1220) provides structural support for holster (724). In the present example, electrical connectors (1230) couple to complementary connectors (not shown) on holster (724) when holster (724) is within holster stand (1220). Power and/or data may be transmitted between holster (724) and recharging dock (1200). In the present example, recharging dock (1200) recharges the power source, such as power source (60), within holster (724) for subsequent procedures. In some versions, recharging dock (1200) may also communicate with control module (750) within holster (724). Such communication may transfer error data and/or usage data to a remote device (such as a user's computer or to a manufacturer's server) for analysis or such communication may be used to reprogram, modify, reset, and/or update control module (750). Still other configurations and operabilities for recharging dock (1200) will be apparent to one of ordinary skill in the art in view of the teachings herein.

B. Exemplary Alternative Tissue Sample Holder

Figure 26:
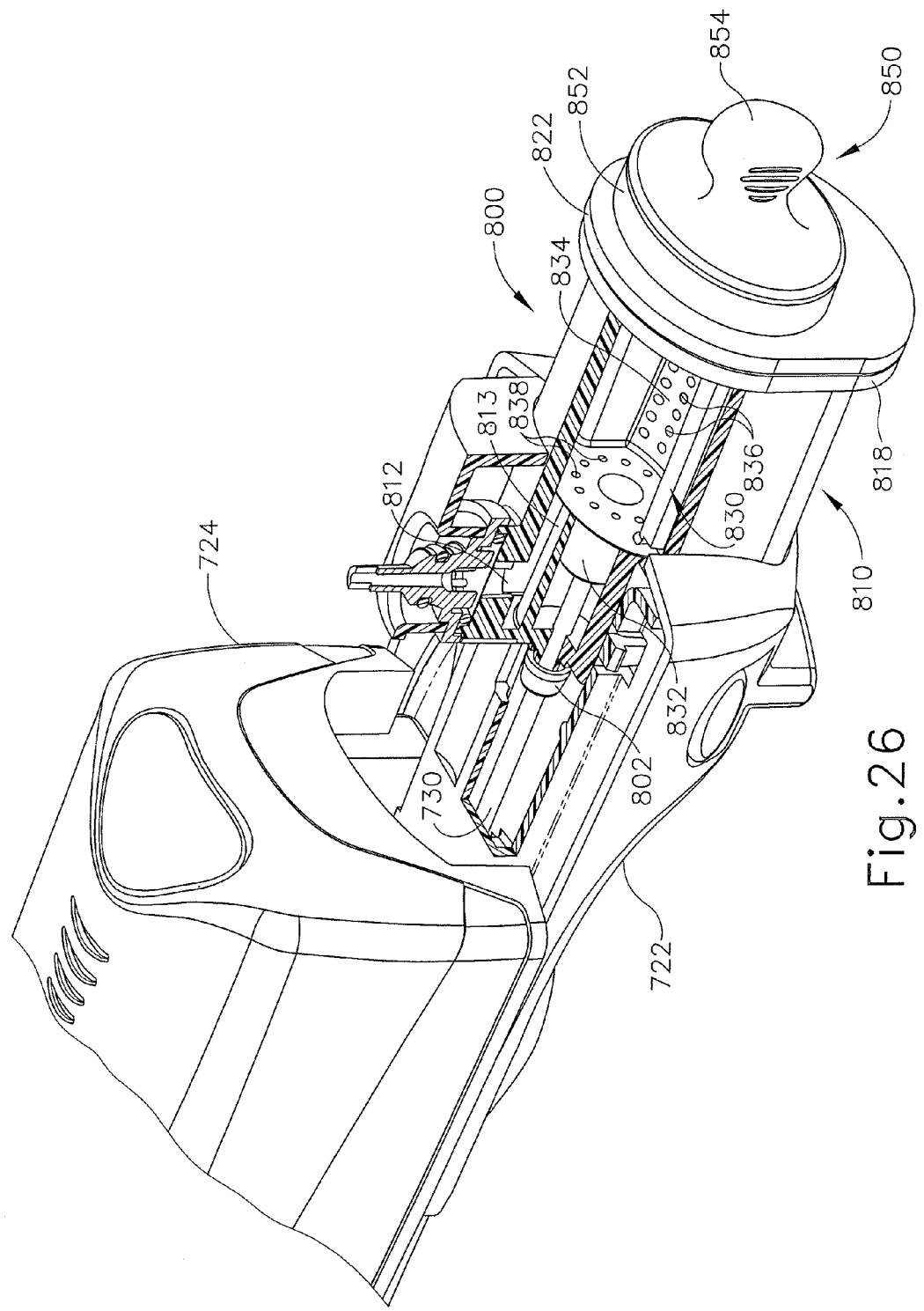
FIG. 26 depicts a rear perspective view of an exemplary alternative tissue sample holder with a portion cut away to reveal a removable tray and other features.
Figure 27:
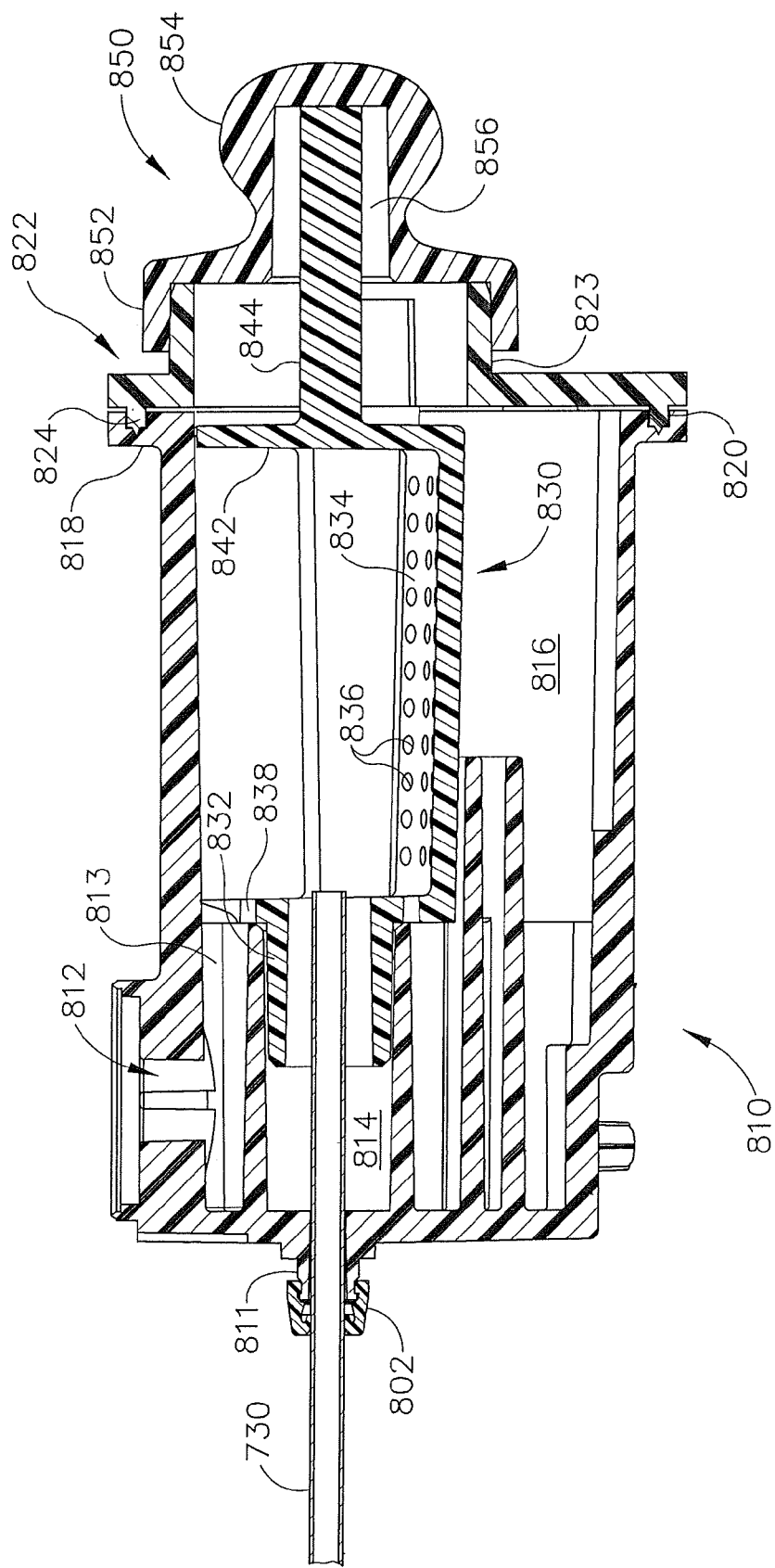
FIG. 27 depicts a cross-sectional view of the alternative tissue sample holder of FIG. 26.
Figure 28:
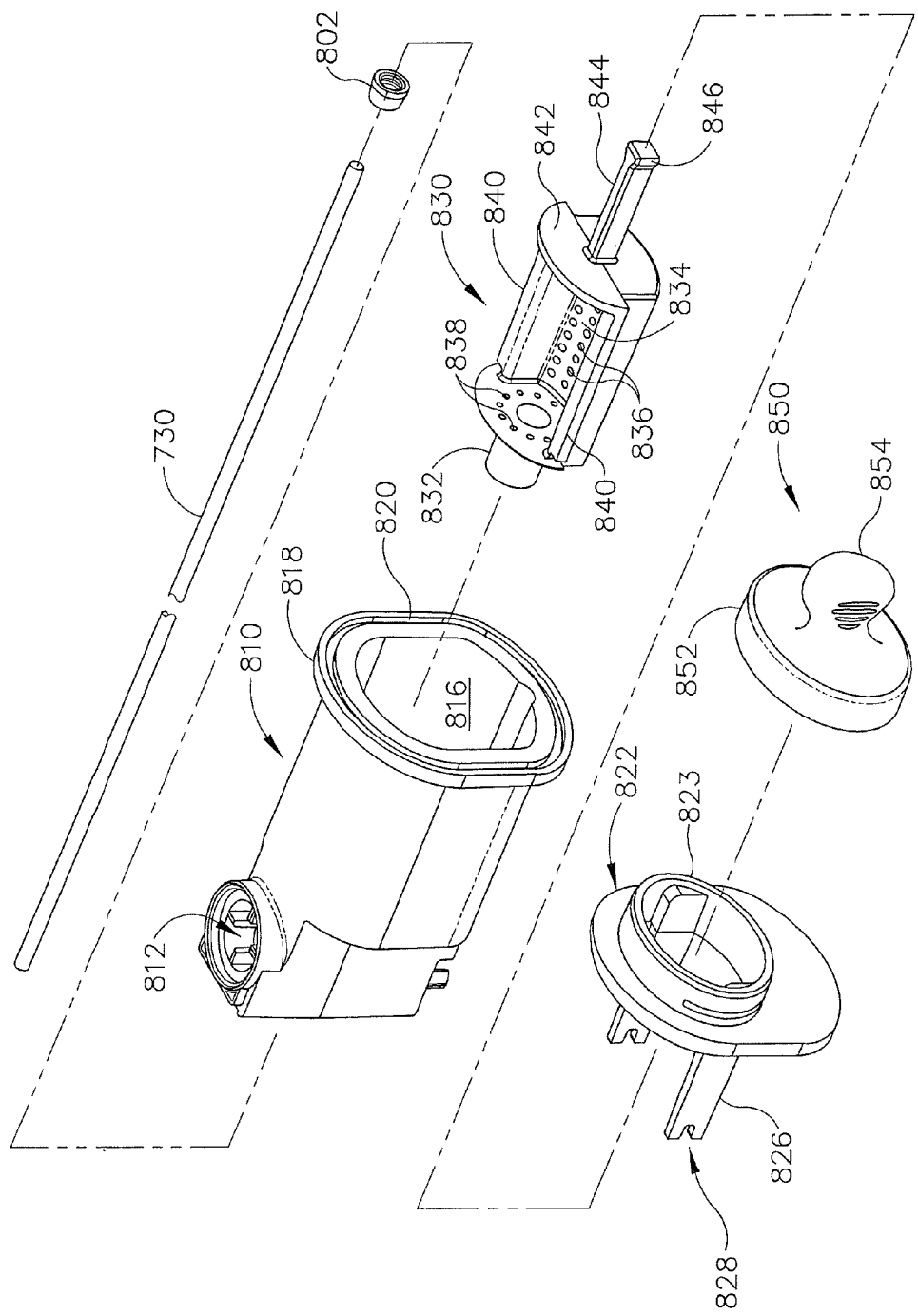
FIG. 28 depicts an exploded perspective view of the tissue sample holder of FIG. 26.

As shown in FIGS. 26-28, tissue sample holder (800) of the present example comprises a cup (810), a tray (830), and a cap (850). In the present example, a cutter seal (802) couples a proximal end of cutter (730) to a distal protrusion (811) of cup (810), thereby forming a substantially fluid seal between cutter (730) and cup (810). Cup (810) includes a vacuum port (812) in fluid communication with a vacuum, such as vacuum source (70) in holster (724). One or more vacuum passages (813) fluidly couple vacuum port (812) to interior (816) of cup (810). Interior (816) of the present example comprises a substantially open region of cup (810) configured to releasably receive tray (830) therein. A recess (814) is formed at a distal end of cup (810) and is configured to receive a distal projection (832) of tray (830) as will be described below. Recess (814) is substantially coaxial to the longitudinal axis of cutter (730). A flange (818) is disposed about the proximal end of cup (810) and is configured to couple to a proximal cover (822). In particular, an annular recess (820) is formed within the proximal face of flange (818) and is configured to couple to an annular projection (824) of proximal cover (822). By way of example only, annular projection (824) and annular recess (820) form an interference fit. Alternatively, screws, bolts, clips, snaps, welds, adhesives, or other coupling items may be used to couple proximal cover (822) to flange (818) Proximal cover (822) further comprises a hollow cylindrical protrusion (823) to which a lip (852) of cap (850) may couple, as described below.

As seen best in FIG. 28, a pair of ledge members (826) extend distally from proximal cover (822) and into interior (816) of cup (810). Ledge members (816) of the present example further include end clips (828) configured to couple to features (not shown) within cup (810) to also couple proximal cover (822) to cup (810). Of course, ledge members (816) and/or proximal cover (822) may be omitted or integrally formed with cup (810). In one merely exemplary instance, proximal cover (822) may be removed when fluid has built up within cup (810). When proximal cover (822) is removed (either by decoupling annular projection (824) from annular recess (820) or otherwise), the interior of cup (810) may be dumped, disposed of, and/or cleaned. Proximal cover (822) may then be reattached to cup (810) and tissue sample collection may continue. Alternatively, proximal cover (822) may be removed with tray (830) and cap (850) when the tissue samples are removed from biopsy device (700) as will be discussed below.

Tray (830) of the present example comprises a distal projection (832), a sample surface (834), a proximal wall (842) and a post (844) extending proximally from the proximal surface of proximal wall (842). As shown best in FIG. 27, distal projection (832) is insertable into recess (814) of cup (810) and receives cutter (730). Sample surface (834) extends proximally from distal projection (832) and, in the present example, is presented by an arcuate member having a plurality of apertures (836) formed therethrough. Sample surface (834) may further include sidewalls extending vertically from the sides of sample surface (834). Sample surface (834) is configured to receive tissue samples on top of sample surface (834) while apertures (836) permit fluid to drop into cup (810). Of course apertures (836) are merely optional and may be omitted. One or more vacuum apertures (838) are provided on a distal wall of tray (830) such that vacuum from vacuum port (812) may be provided through vacuum passages (813), through vacuum apertures (838) and into interior (816). As noted in the aforementioned examples, the application of vacuum pulls the tissue samples through the cutter lumen and into tissue sample holder (800).

As noted above, tray (830) further comprises proximal wall (842) with a post (844) extending proximally therefrom. Post (844) of the present example is a rectangular member configured to be grasped by an inner region (856) of cap (850), as will be discussed below. It should be understood, though, that post (844) may include other geometries, including cylindrical projections, pyramidal projections, pentagonal prisms, and/or other configurations. Post (844) of the present example further includes a flared portion (846) at the proximal end of post (844). Tray (830) also includes a pair of shoulders (840), shown best in FIG. 28. Shoulders (840) are configured to rest atop ledge members (826) of proximal cover (822) such that tray (830) is supported, at least in part, by proximal cover (822). Shoulders (840), ledge members (826), end clips (828) and the features end clips (828) couple to in cup (810) may assist in aligning distal projection (832) with the proximal end of cutter (730) when inserting tray (830) and/or proximal cover (822) into cup (810).

Cap (850) is coupled to proximal cover (822) and includes a distally extending lip (852), a handle (854), and an inner region (856) formed within the distal end of handle (854) and into which flared portion (846) of post (844) is inserted. Cap (850) of the present example is formed of a flexible material, such as a rubber or semi-rigid plastic. Lip (852) is couplable to hollow cylindrical protrusion (823) of proximal cover (822) and is configured to fluidly seal cap (850) to proximal cover (822). In one merely exemplary configuration, lip (852) frictionally fits to proximal cover (822). Handle (854) is configured to be gripped by a user such that inner region (856) of handle (854) may be compressed against flared portion (846) to grip post (844).

Once a user has collected the desired tissue samples, the user grips handle (854) to compress inner region (856) about flared portion (846) of post (844). The user then pulls proximally on handle (854) to remove tray (830) from within cup (810). With cap (850) and tray (830), the user may then maneuver tray (830) above a sample container, such as sample container (300), and release the squeezing pressure on handle (854) without necessarily dropping cap (850). With the release of pressure, inner region (856) resiliently expands to permit flared portion (846) to slide out of inner region (856). The user maintains a grip on handle (854) to hold onto cap (850) while tray (830) then falls away into the sample container. The user may then grip flared portion (846) of another tray (830) to be inserted into cup (810) for use with biopsy device (700). In one merely exemplary alternative, proximal cover (822) may be detachable from cup (810) such that tray (830), proximal cover (822), and cap (850) are removed together. Removal of proximal cover (822) with tray (830) and cap (850) may permit tray (830) to rest upon ledge members (826) when tray (830) is being transported.

Still other configurations for cup (810), tray (830), and cap (850) will be apparent to one of ordinary skill in the art in view of the teachings herein.

C. Exemplary Plug Adapter

Figure 29:
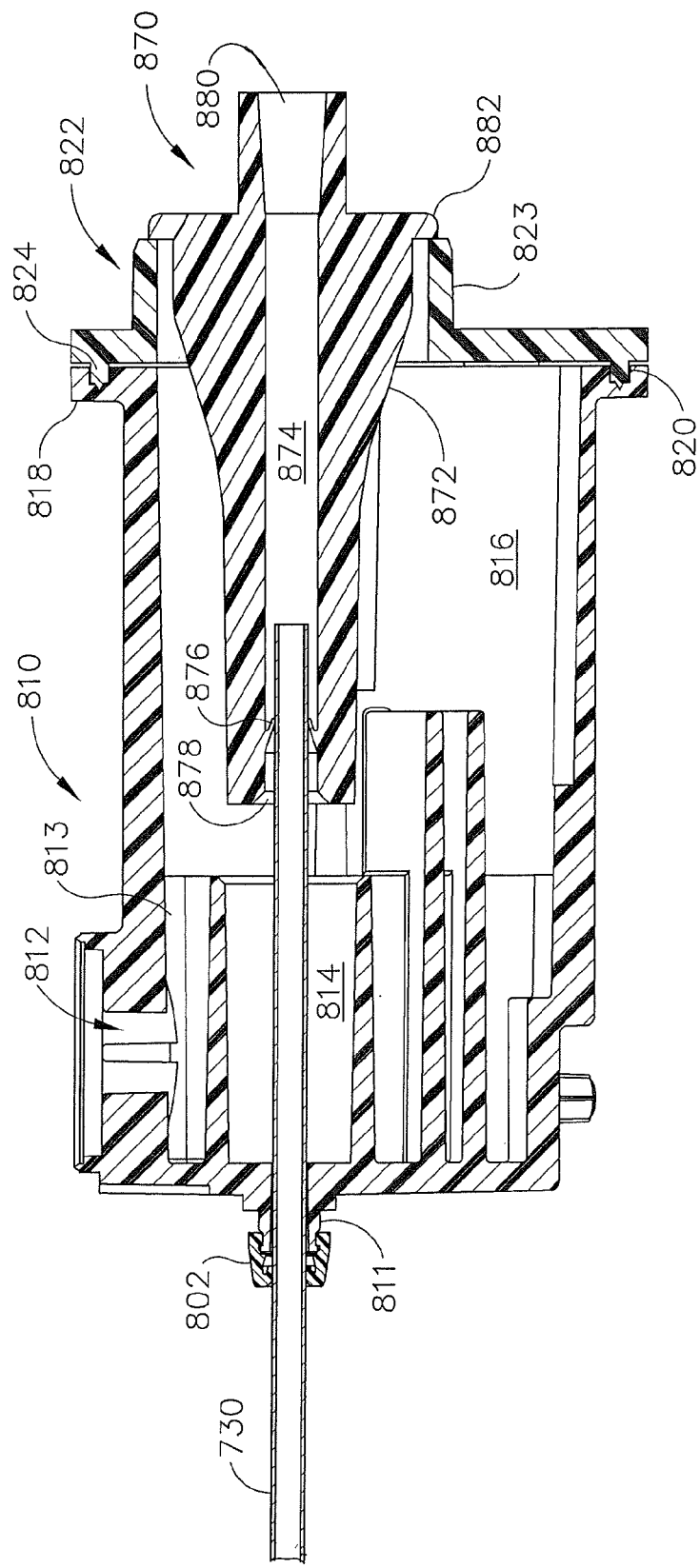
FIG. 29 depicts a cross-sectional view of the tissue sample holder of FIG. 26, with a plug adapter in place of the removable tray.
Figure 30:
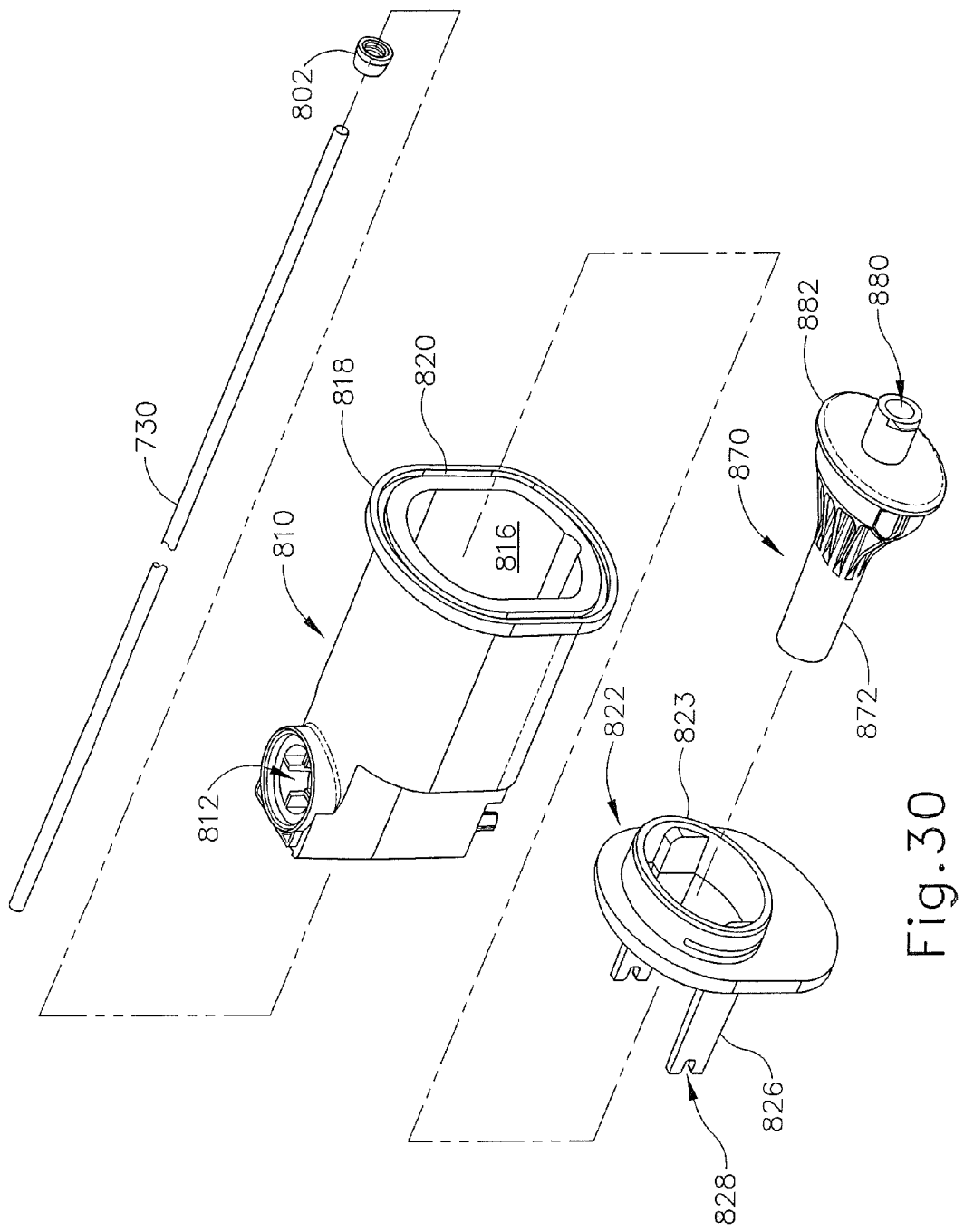
FIG. 30 depicts an exploded perspective view of the tissue sample holder and plug adapter of FIG. 29.

Once cap (850) and tray (830) have been removed from cup (810), it may be preferable to a user to mark and/or deliver other medicinal items to the biopsy cavity formed within the patient's tissue. Accordingly, a plug adapter may be useful to couple to cutter (730) within cup (810). As shown in FIG. 29-30, an exemplary plug adapter (870) may be used with cup (810) described above. Plug adapter (870) includes a body (872), a plug lumen (874) formed longitudinally through body (872), and a seal (876) disposed within the plug lumen (874). Funnels (878, 880) are formed on both the proximal end of plug lumen (874) (funnel (880)) and the distal end of plug lumen (874) (funnel (878)). Funnel (878) is configured to aid the insertion of cutter (730) into plug adapter (870), as shown in FIG. 29, during insertion of plug adapter (870) in cup (810). Funnel (880) is configured to aid the insertion of a marker deployer, such as marker deployer (1000), into the proximal end of plug adapter (870). Plug adapter (870) further includes an annular shoulder (882) that abuts the proximal end of hollow cylindrical protrusion (823) when plug adapter (870) is inserted therein. In this configuration, plug adapter (870) provides a tubular passageway between the proximal end of cutter (730) and the exterior of proximal cover (822) such that a marker deployer may be more easily inserted into cutter (730). Seal (876) fluidly couples to and seals cutter (730) to plug adapter (870) such that any fluid within plug lumen (874) does not enter cup (810). Of course, plug adapter (870) may be omitted and the marker deployer may be guided to the proximal end of cutter (730) within cup (810).

In some versions, a medicinal fluid (e.g., pain medications, coagulants, etc.) may be contained within a syringe (not shown) having a distal tube (not shown) that is insertable into plug adapter (870). Plug lumen (874) and/or funnel (880) may be sized such that a seal is formed between plug lumen (874) and/or funnel (880) and the distal tube of the syringe when the distal tube is inserted into plug lumen (874) and/or funnel (880). With seal (876) fluidly coupled to cutter (730), the user may inject the fluid contained within the syringe into plug lumen (874) without having the fluid enter cup (810). Instead, with cutter (730) in a proximally retracted position, the fluid travels through cutter (730) and out through lateral aperture (23) to the biopsy site. Of course other arrangements for seal (876) and/or cutter (730) will be apparent to one of ordinary skill in the art in view of the teachings herein.

In one merely exemplary alternative configuration, funnel (880) may be configured as a leur lock or a pierceable membrane such that a syringe or needle with medicinal fluid may be delivered through plug adapter (870) to cutter (730) and, ultimately, out into the biopsy cavity. Lumen (874) may also include one or more features configured to prevent fluid from being communicated proximally through lumen (874), while still allowing a marker applier cannula or other type of device to pass distally through lumen (874). This may reduce the likelihood of bodily fluids leaking proximally through cutter (730) and thus proximally through lumen (874). Still other configurations and uses for plug adapter (870) will be apparent to one of ordinary skill in the art in view of the teachings herein.

D. Another Exemplary Tissue Sample Holder

Figure 31:
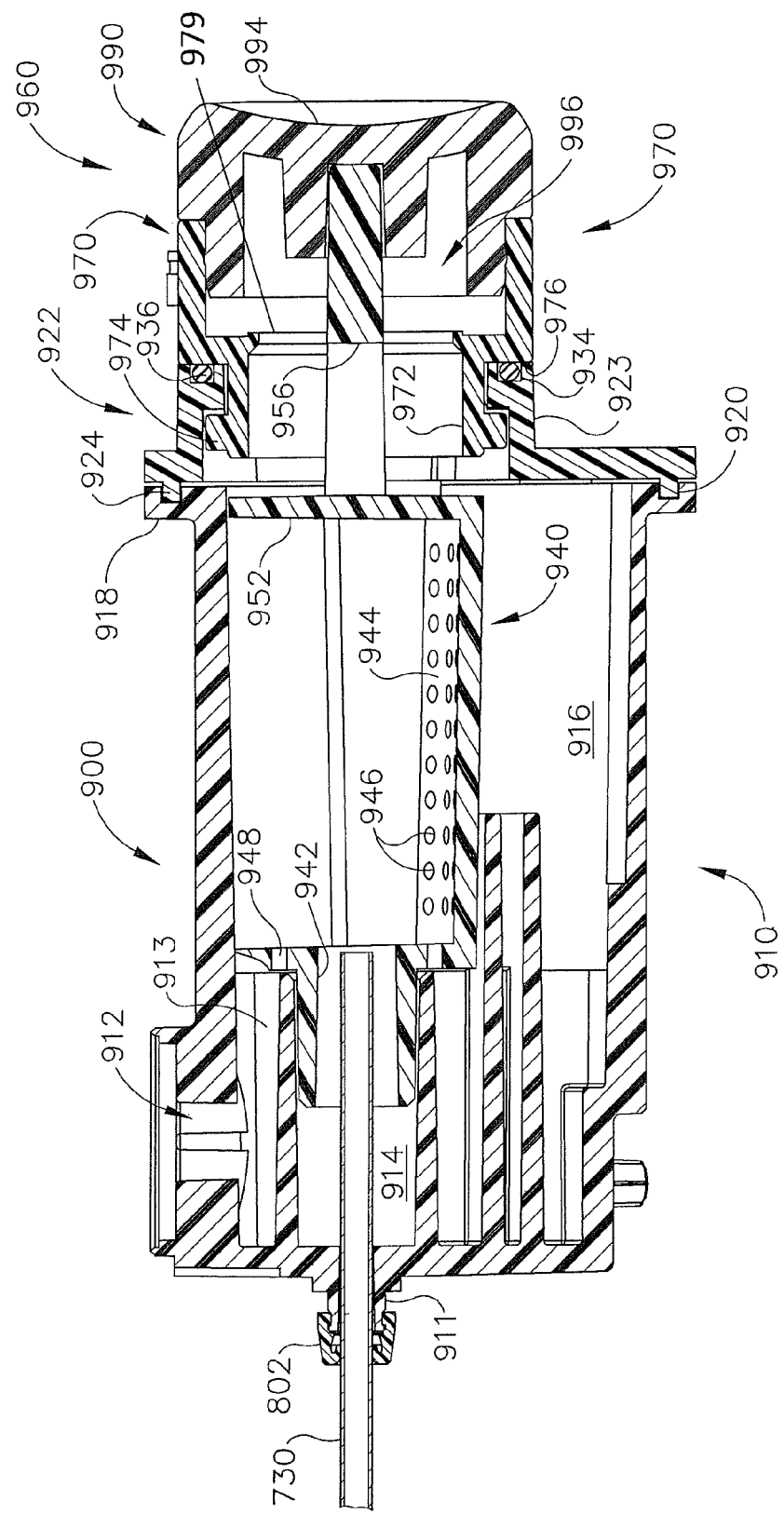
FIG. 31 depicts a cross-sectional view of still another exemplary tissue sample holder, with a removable tray.
Figure 32:
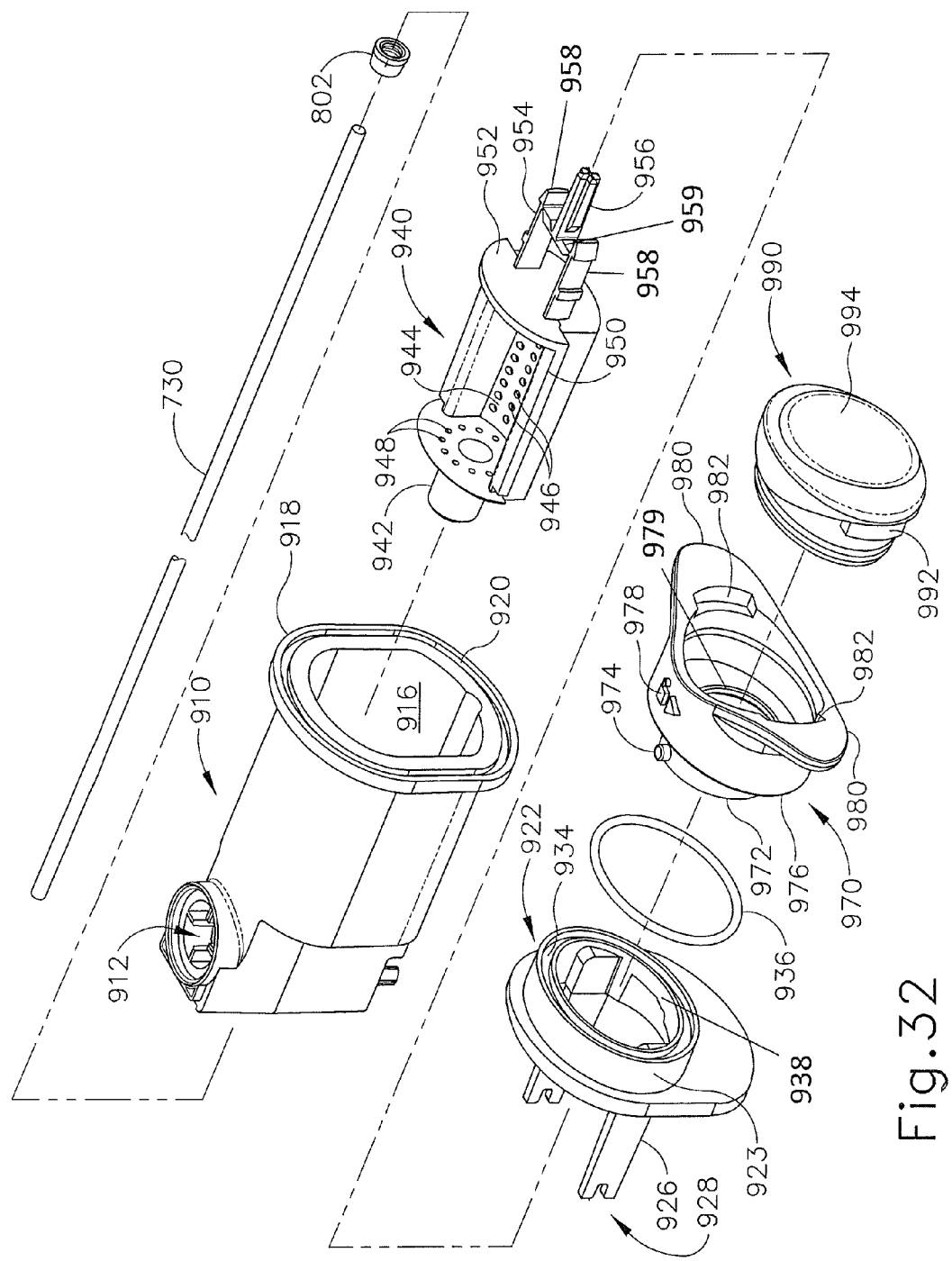
FIG. 32 depicts an exploded perspective view of the tissue sample holder of FIG. 31.

FIGS. 31-32 depict yet another exemplary tissue sample holder (900) having a cup (910), a tray (940), and a cap (960). In the present example, cutter seal (802) couples a proximal end of cutter (730) to a distal protrusion (911) of cup (910), thereby forming a substantially fluid seal between cutter (730) and cup (910). Cup (910) includes a vacuum port (912) in fluid communication with a vacuum, such as vacuum source (70). One or more vacuum passages (913) fluidly couple vacuum port (912) to interior (916) of cup (910). Interior (916) of the present example comprises a substantially open region of cup (910) configured to releasably receive tray (940) therein. A recess (914) is formed at a distal end of cup (910) and is configured to receive a distal projection (942) of tray (940) as will be described below. Recess (914) is substantially coaxial to the longitudinal axis of cutter (730). A flange (918) is disposed about the proximal end of cup (910) and is configured to couple to a proximal cover (922). In particular, an annular recess (920) is formed within the proximal face of flange (918) and is configured to couple to an annular projection (924) of proximal cover (922). By way of example only, annular projection (924) and annular recess (920) form an interference fit. Alternatively, screws, bolts, clips, snaps, welds, adhesives, or other coupling items may be used to couple proximal cover (922) to flange (918). Proximal cover (922) further comprises a hollow cylindrical protrusion (923) having a lock path (938) formed on the interior surface of hollow cylindrical protrusion (923). Lock path (938) is a helical recess or channel formed within the interior surface of hollow cylindrical protrusion (923) and is configured to retain locking nubs (974), as will be described below, similar to a bayonet mounting slot. An outer annular recess (934) is also formed in hollow cylindrical protrusion (923) and an o-ring (936) is inserted into the outer annular recess (934) to seal hollow cylindrical protrusion (923) to a shoulder portion (976) of a locking adapter (970), described below.

As seen best in FIG. 32, a pair of ledge members (926) extend distally from proximal cover (922) and into interior (916) of cup (910). Ledge members (926) of the present example further include end clips (928) configured to couple to features (not shown) within cup (910) to also couple proximal cover (922) to cup (910). Of course, ledge members (926) and/or proximal cover (922) may be omitted or integrally formed with cup (910). In one merely illustrative example, proximal cover (922) may be removed when fluid has built up within cup (910). When proximal cover (922) is removed (either by decoupling annular projection (924) from annular recess (920) or otherwise), the interior of cup (910) may be dumped, disposed of, and/or cleaned. Proximal cover (922) may then be reattached to cup (910) and tissue sample collection may continue. Alternatively, proximal cover (922) may be removed with tray (940) and cap (960) when the tissue samples are removed from the biopsy device (700) as will be discussed below.

Tray (940) of the present example comprises a distal projection (942), a sample surface (944), a proximal wall (952) and a release member (954) extending proximally from the proximal surface of proximal wall (952). As shown best in FIG. 31, distal projection (942) is insertable into recess (914) of cup (910) and receives cutter (730). Sample surface (944) extends proximally from distal projection (942) and, in the present example, is presented by an arcuate member having a plurality of apertures (946) formed therethrough. Sample surface (944) may further include sidewalls extending vertically from the sides of sample surface (944). Sample surface (944) is configured to receive tissue samples on top of sample surface (944) while apertures (946) permit fluid to drop into cup (910). Of course apertures (946) are merely optional and may be omitted. One or more vacuum apertures (948) are provided on a distal wall of tray (940) such that vacuum from vacuum port (912) may be provided through vacuum passages (913), through vacuum apertures (948) and into interior (916). As noted in the aforementioned examples, the application of vacuum pulls the tissue samples through the cutter lumen and into tissue sample holder (900). Tray (940) further comprises proximal wall (952) with a release member (954) extending proximally therefrom. Release member (954) of the present example includes a cross-shaped post (956) insertable into an inner region (996) of push release member (990) of cap (960), as will be discussed below. It should be understood, though, that post (956) may include other geometries, including cylindrical projections, pyramidal projections, pentagonal prisms, and/or other configurations. Release member (954) further comprises a pair of resilient latches (958), shown in FIG. 32, that are configured to selectively couple to a circumferential ledge (979) on the interior of a locking adapter (970), as will be described in more detail below. Resilient latches (958) of the present example are coupled to a cross member (959) that is configured to bow distally when post (956) is pressed distally by the user. Accordingly, resilient latches (958) bend inwardly and decouple from circumferential ledge (979) when cross member (959) bows distally. Tray (940) also includes a pair of shoulders (950), shown best in FIG. 32. Shoulders (950) are configured to rest atop ledge members (926) of proximal cover (922) such that tray (940) is supported, at least in part, by proximal cover (922). Shoulders (950), ledge members (926), end clips (928) and the features end clips (928) couple to in cup (910) may assist in aligning distal projection (942) with the proximal end of cutter (730) when inserting tray (940) and/or proximal cover (922) into cup (910).

Cap (960) of the present example comprises a two-piece assembly comprising a locking adapter (970) and a push release member (990). As best seen in FIG. 32, locking adapter (970) includes a cylindrical projection (972) having one or more locking nubs (974), a shoulder portion (976), a circumferential ledge (979) formed on the interior of locking adapter (970), a pair of finger grips (980), and a pair of tab recesses (982). Cylindrical projection (972) and locking nubs (974) are insertable into gaps of the lock path or channel formed in proximal cover (922). With nubs (974) inserted a sufficient distance, a user rotates locking adapter (970) such that nubs (974) helically follow the lock path until shoulder portion (976) of locking adapter (970) abuts proximal cover (922). One or more detents may be provided within the lock path to secure nubs (974) at this position, similar to a bayonet mount. Shoulder portion (976) extends proximally from cylindrical projection (972) and then radially outwardly to form an L-shaped revolute portion. The bottom of shoulder portion (976) compresses o-ring (936) when nubs (974) are at the end of their respective lock paths, thereby fluidly sealing locking adapter (970) to proximal cover (922). Shoulder portion (976) may further include an indicator (978) to indicate the unlocking/locking rotation necessary to decouple/couple locking adapter (970) to proximal cover (922). Circumferential ledge (979) is disposed on the interior of the L-shaped revolute portion and is configured to selectively secure tray (940) when resilient latches (958) engage circumferential ledge (979). Flared finger grips (980) extend from the proximal end of shoulder portion (976) and are configured to be gripped by one or more fingers of a user. In the present example, two recesses (982) are formed within finger grips (980) and are configured to receive tabs (992) of push release member (990), described below.

Push release member (990) comprises a flexible member having a pair of tabs (992), an inner region (996), and a flexible button (994) opposite inner region (996). Push release member (990) is insertable into locking adapter (970) with tabs (992) inserting into recesses (982). An adhesive may be provided to secure tabs (992) in recesses (982). Inner region (996) is configured to receive and frictionally retain post (956) therein. When flexible button (994) is depressed against inner region (996), post (956) is actuated distally relative to push release member (990). As noted previously, when post (956) is actuated distally, cross member (959) bows distally, thereby bending resilient latches (958) inwardly toward post (956). Accordingly, resilient latches (958) of tray (940) detach from locking adapter (970), and post is expelled out of inner region (996). Thus, tray (940) is detachable from cap (960).

Once a user has collected the desired tissue samples, the user grips finger grips (980) of locking adapter (970) and rotates locking adapter (970) until nubs (974) are aligned with the longitudinal gaps of proximal cover (922). With nubs (974) and the gaps aligned, the user then pulls proximally on cap (960) to remove tray (940) from within cup (910). With cap (960) and tray (940), the user may then maneuver tray (940) above a sample container, such as sample container (300), and push flexible button (994) distally to disengage resilient latches (958) and to dislodge post (956) from within inner region (996). Post (956) then slides out of inner region (996) and tray (940) then falls away into the sample container. The user may continue to grip finger grips (980) to align and insert post (956) of another tray (940) to be inserted into cup (910) for use with biopsy device (700).

Still other configurations for cup (910), tray (940), and cap (960) will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for use in a biopsy procedure, wherein the device comprises:
   a. a body portion;
   b. a needle, wherein the needle extends distally from the body portion, wherein the needle includes:
      i. an outer cannula defining an inner lumen,
      ii. a tip, and
      iii. a lateral aperture configured to receive tissue, wherein the lateral aperture is proximal to the tip;
   c. a cutter, wherein the cutter is operably configured to translate relative to the needle to sever a tissue specimen from tissue received within the lateral aperture; and
   d. a tissue sample holder, wherein the tissue sample holder is configured to receive tissue specimens severed by the cutter, wherein the tissue sample holder includes:
      i. an outer cup, wherein the outer cup defines an interior space, wherein the outer cup has a distal end and a proximal end, wherein the outer cup further includes a vacuum port located at the distal end, wherein the vacuum port is configured to couple with a vacuum source,
      ii. a cap, wherein the cap is selectively coupled with the proximal end of the outer cup, wherein the cap has at least one ejection feature, wherein the at least one ejection feature extends proximally from the cap when the tray is disposed in the outer cup, wherein a proximal end of the cap is closed by the at least one ejection feature, and
      iii. a tray, wherein the tray is configured to hold the severed tissue specimens, wherein the tray is selectively coupled with the cap by an interior receiving member of the cap, wherein the tray includes a pair of resilient latches and a post disposed between the resilient latches, wherein the interior receiving member of the cap is configured to grip the resilient latches, wherein the tray is configured to be ejected distally from the cap when the post of the tray is acted upon by the at least one ejection feature of the cap to thereby release the pair of resilient latches from the grip of the interior receiving member.

2. The device of claim 1, wherein the tray includes a proximal end, wherein configurations of the proximal end of the tray and the interior receiving member complement one another to provide an interference fitting between the proximal end of the tray and the interior receiving member.

3. The device of claim 1, wherein the cap further includes a button, wherein the interior receiving member extends proximally into the button, and wherein the post is insertable into the interior receiving member of the cap.

4. The device of claim 3, wherein the cross-sectional area of the interior receiving member is greater than the cross-sectional area of the post.

5. The device of claim 4, wherein the button has a deformable material.

6. The device of claim 1, wherein the cap further includes a push release button defining the at least one ejection feature and the interior receiving member, and wherein the post is insertable into an inner region defined by one or more distal extensions from the push release button.

7. The device of claim 6, wherein the push release button is a flexible button, wherein the post is selectively releasable from the push release button by depressing the flexible button.

8. The device of claim 6, further including a locking adapter coupled to the push release button and selectively coupleable to the outer cup.

9. The device of claim 1, wherein the tray has a sample surface, a proximal end, and a pair of side portions, wherein the sample surface extends distally from the proximal end between the pair of side portions, wherein the sample surface includes a plurality of openings configured to drain fluid from the tray.

10. The device of claim 9, wherein the tray is a transparent plastic material.

11. The device of claim 1, wherein the cap is selectively coupled with the outer cup by a cover including one or more ledge members, and wherein the cap has one or more locking nubs configured to engage a complementary recess of the cover.

12. The device of claim 1, wherein the cap includes a port providing selective fluid communication through the cap.

13. A device for use in a biopsy procedure, wherein the device comprises:
 a. a body portion;
 b. a needle, wherein the needle extends distally from the body portion, wherein the needle includes:
  i. an outer cannula defining an inner lumen,
  ii. a tip, and
  iii. a lateral aperture configured to receive tissue, wherein the lateral aperture is proximal to the tip;
 c. a cutter, wherein the cutter is operably configured to translate relative to the needle to sever a tissue specimen from tissue received within the lateral aperture; and
 d. a tissue sample holder, wherein the tissue sample holder is configured to receive tissue specimens severed by the cutter, wherein the tissue sample holder includes:
  i. an outer cup, wherein the outer cup defines an interior space,
  ii. a tissue tray removably received in the interior space of the cup, wherein the tissue tray includes a release member extending proximally from the tissue tray, wherein the release member has a pair of resilient latches and a cross member extending between the resilient latches, and
  iii. a deformable cap removably secured relative to the outer cup, wherein the cap has a flexible button portion, wherein the flexible button portion is configured to close a proximal end of the cap, wherein the flexible button portion fully encompasses a portion of the resilient latches, wherein the flexible button portion is operable to actuate the release member of the tissue tray to selectively release the tissue tray from the deformable cap.

14. The device of claim 13, wherein the cap is deformable to selectively engage the outer cup.

15. The device of claim 13, wherein the tissue tray and cap are removable together from the outer cup as an assembly.

16. A method of operating a biopsy device, wherein the biopsy device includes a cannula, a cutter, and a tissue sample holder, wherein the cannula includes a transverse tissue receiving aperture, wherein the cutter is configured to sever samples from tissue received through the transverse tissue receiving aperture, wherein the tissue sample holder is configured to receive one or more tissue samples severed by the cutter, wherein the tissue sample holder includes a chamber, a tray disposed in the chamber, wherein the tray has a pair of resilient latches and a cross member extending between the resilient latches, and a cap releasably engageable with the tray, wherein the cap includes a flexible portion, wherein the flexible portion defines an inner region, the method comprising:
 (a) actuating the cutter to sever at least one tissue sample;
 (b) communicating the at least one tissue sample to the tray of the tissue sample holder, wherein the proximal end of the tissue sample holder is closed by the cap during the act of communicating the at least one tissue sample to the tray;
 (c) removing the cap, the tray, and the at least one tissue sample together from the chamber; and
 (d) releasing the tray from the cap by pressing distally on the flexible portion of the cap to thereby force the tray distally away from the cap, wherein the act of pressing distally on the flexible portion deforms the cross member of the tray to disengage the resilient latches of the tray from the inner region of the flexible portion.

17. The method of claim 16, wherein the act of releasing the tray from the cap is performed with a single hand, without grasping the tray with another hand.

18. The method of claim 16, further including:
 (a) inserting a plug into the chamber after the cap, the tray, and the at least one tissue sample are removed from the chamber, wherein the plug defines a lumen aligned with the cutter; and
 (b) inserting an instrument through the lumen of the plug and into the cutter.

* * * * *